(12) United States Patent
Hagihira et al.

(10) Patent No.: US 11,471,613 B2
(45) Date of Patent: Oct. 18, 2022

(54) SYRINGE NEEDLE REMOVAL APPARATUS

(71) Applicants: THREE DYNE CO., LTD., Yatsushiro (JP); NATIONAL UNIVERSITY CORPORATION KUMAMOTO UNIVERSITY, Kumamoto (JP)

(72) Inventors: Koji Hagihira, Yatsushiro (JP); Yoshitaka Nakanishi, Kumamoto (JP); Kazuma Shibata, Kumamoto (JP)

(73) Assignees: THREE DYNE CO., LTD., Kumamoto (JP); NATIONAL UNIVERSITY CORP. KUMAMOTO UNIVERSITY, Kumamoto (JP)

( * ) Notice: Subject to any disclaimer, the term of this patent is extended or adjusted under 35 U.S.C. 154(b) by 302 days.

(21) Appl. No.: 16/954,462

(22) PCT Filed: Dec. 7, 2018

(86) PCT No.: PCT/JP2018/045193
§ 371 (c)(1),
(2) Date: Jun. 16, 2020

(87) PCT Pub. No.: WO2019/124124
PCT Pub. Date: Jun. 27, 2019

(65) Prior Publication Data
US 2021/0162137 A1 Jun. 3, 2021

(30) Foreign Application Priority Data

Dec. 18, 2017 (JP) .............................. JP2017-241730
Apr. 12, 2018 (JP) .............................. JP2018-076940

(51) Int. Cl.
*A61M 5/32* (2006.01)
(52) U.S. Cl.
CPC ... *A61M 5/3205* (2013.01); *A61M 2005/3206* (2013.01); *A61M 2005/3208* (2013.01)

(58) Field of Classification Search
CPC .............. A61M 5/3204; A61M 5/3205; A61M 5/3276; A61M 2005/3206; A61M 2005/3208; Y10T 29/53961
See application file for complete search history.

(56) References Cited

U.S. PATENT DOCUMENTS

| 4,986,811 A * | 1/1991 | Thead ................. A61M 5/3205 604/110 |
| 5,312,346 A * | 5/1994 | Han .................... A61M 5/3205 604/110 |

(Continued)

FOREIGN PATENT DOCUMENTS

| JP | H07-464 | 1/1995 |
| JP | 2001-25494 | 1/2001 |

(Continued)

OTHER PUBLICATIONS

PCT/JP2018/045193, International Search Report and Written Opinion, 4 pages—English, 6 pages—Japanese.

*Primary Examiner* — Nathan R Price
*Assistant Examiner* — Justin L Zamory
(74) *Attorney, Agent, or Firm* — Andrew F. Young; Nolte Lackenbach Siegel

(57) ABSTRACT

The injection needle removal device has: a cylindrical outer cylinder on an upper opening of an injection needle case; a helical track on an inner peripheral surface of the outer cylinder in a helical shape from an upper locking point to a lower locking point; a syringe holding cylinder helically advances in the outer cylinder along the helical track; an injection needle tightening ring on a lower end portion of the syringe holding cylinder, the injection needle tightening ring holds an injection needle base portion of a syringe in the syringe holding cylinder to clamp the injection needle base portion; and a locking mechanism that stops the syringe holding cylinder where the injection needle tightening ring (Continued)

is exposed from a lower side of the outer cylinder at the lower locking point. The injection needle tightening ring turns to remove the syringe needle base portion from the syringe body and to expand in a distal-end divided manner by a turning generated by a descending movement of the syringe holding cylinder proximate the lower locking point to discard the injection needle base portion into the injection needle accommodation case with the injection needle.

7 Claims, 30 Drawing Sheets

(56) References Cited

U.S. PATENT DOCUMENTS

| 5,573,113 | A | * | 11/1996 | Shillington | A61M 5/3205 |
|---|---|---|---|---|---|
| | | | | | 206/370 |
| 5,947,950 | A | * | 9/1999 | Shillington | A61M 5/3205 |
| | | | | | 206/370 |
| 2012/0145577 | A1 | * | 6/2012 | Bode | A61M 5/3276 |
| | | | | | 414/431 |
| 2015/0007425 | A1 | * | 1/2015 | Dasbach | A61M 5/3205 |
| | | | | | 29/281.1 |

FOREIGN PATENT DOCUMENTS

| JP | 2009-225825 | 10/2009 |
|---|---|---|
| JP | 2012-525173 | 10/2012 |
| JP | 3196419 | 2/2015 |
| JP | 2015-509412 | 3/2015 |

\* cited by examiner

SYRINGE NEEDLE REMOVAL APPARATUS

CROSS REFERENCE TO RELATED APPLICATIONS

This application relates to and claims priority from PCT Ser. No.:PCT/JP2018/045193 filed Dec. 7, 2018, the entire contents of which is incorporated herein by reference. This application also claims the priority of Japanese Patent Application No. 2018-076940 filed Apr. 12, 2018 and Japanese Patent Application No. 2017-241730 filed Dec. 18, 2017.

FIGURE SELECTED FOR PUBLICATION

FIG. 3

TECHNICAL FIELD

The present invention relates to an injection (syringe) needle removable device for removing an injection needle from a syringe.

BACKGROUND ART

Conventionally, with respect to an injection needle after an injection operation is performed, a medical worker pinches an injection needle base portion threadedly mounted on a distal end of a syringe body and rotates the injection needle base portion. With such an operation for removing the injection needle from the syringe body, an infectious medical waste is discarded.

In such a removal operation, it is necessary for a medical worker to bring his finger tip to an injection needle and hence, there is a danger that an erroneous pricking accident where the injection needle erroneously pricks a finger occurs.

Such an erroneous pricking accident (incident) gives rise to a concern that a medical worker who has many chances of performing an operation of removing an injection needle is infected by an infectious disease with which a patient is infected and hence, an extremely serious problem occurs.

To avoid such an erroneous pricking accident there has been proposed a needle removal device capable of performing a removal operation by which an injection needle can be removed from a syringe without bringing a finger close to the injection needle (see patent literature 1, for example).

Such a needle removal device includes: a needle removal cylindrical body; and a needle removal spinning body which is rotatably housed in the cylindrical body, and threadedly removed from an injection needle base portion from a syringe body by helically turning the injection needle base portion in such a manner that the needle removal spinning body is engaged with an outer periphery of the injection needle base portion having an injection needle by fitting and the needle removal spinning body is rotated in the needle removal cylindrical body. In such a needle removal device, the injection needle base portion is threadedly removed from the syringe body along with the rotation of the needle removal spinning body, and the needle removal spinning body is descended as it is, and the needle removal spinning body and the injection needle base portion which holds the needle removal spinning body are made to fall together into an injection needle accommodating case provided as a separate member.

PRIOR ART LITERATURE

Patent Literature

[Patent literature 1] Japanese registered utility model 3196419

SUMMARY OF INVENTION

Problems to be Solved by Invention

However, in the above-mentioned conventional needle removal device, each time an operation of removing a used injection needle is performed, it is necessary to mount the needle removal spinning body in the needle removal cylindrical body and hence, the number of operation steps is increased thus giving rise to a drawback that the removal operation is cumbersome.

Further, it is necessary to discard the needle removal spinning body in the injection needle accommodating (housing) case together with an injection needle and hence, each time the removal operation is performed, the needle removal spinning body is used as an expendable (disposable) article. Accordingly, there arises the following drawbacks. That is, such a removal operation is disadvantageous in terms of cost, and the number of useless medical wastes is increased.

Means for Solving Problems

To overcome the above-mentioned problem, (1) an injection needle removal device according to the present includes: a cylindrical outer cylinder which is mountable on an upper opening of an injection needle accommodation case; a helical track which is formed on an inner peripheral surface of the outer cylinder in a helical shape from an upper locking point to a lower locking point; a syringe holding cylinder having a cylindrical shape which turns and helically advances in the outer cylinder along the helical track; an injection needle tightening ring which is disposed on a lower end portion of the syringe holding cylinder, the injection needle tightening ring capable of holding an injection needle base portion of a syringe inserted into the syringe holding cylinder while capable of clamping the injection needle base portion; and a locking mechanism which stops the syringe holding cylinder in a state where the injection needle tightening ring is exposed from a lower side of the outer cylinder at the lower locking point, wherein the injection needle tightening ring is configured to remove the syringe needle base portion from the syringe body due to turning of the syringe holding cylinder, and to expand in a distal-end divided manner due to a turning force generated by a descending movement of the syringe holding cylinder in a vicinity of the lower locking point thus discarding the injection needle base portion into the injection needle accommodation case together with the injection needle.

The injection needle removal device according to the present invention also has the following technical features.

(2) Turning and helical-advancing of the syringe holding cylinder is realized by bringing a projection formed on an outer peripheral surface of the syringe holding cylinder into slide contact with a helical groove which is formed on an inner peripheral surface of the outer cylinder as the helical track, and upper and lower tapered surfaces, which are expanded inward in a radial direction of the outer cylinder, are formed on the helical groove, and the projection is formed of a projection having a circular arcuate surface on a distal end thereof, and the projection is brought into point contact with the tapered surfaces so as to reduce a sliding resistance generated at the time of helically turning advancing the syringe holding cylinder is reduced.

(3) The projection is formed of a plurality of projections which are formed on the outer peripheral surface of the syringe holding cylinder, and plurality of projections are brought into slide contact with the helical groove.

(4) The injection needle tightening ring is formed of a plurality of divided members which are pivotally mounted on a lower portion of a cylindrical syringe holding cylinder body which forms the syringe holding cylinder in an expandable manner.

(5) A grip means which generates a friction force against an operation of removing the syringe body from the syringe holding cylinder is provided to an inner wall of the syringe holding cylinder which oppositely faces the syringe body.

(6) The injection needle removal device further includes a biasing mechanism which biases the syringe holding cylinder upward in the outer cylinder.

(7) The outer cylinder has a double cylindrical structure formed of an outer cylinder and an inner cylinder disposed on a same axis, the helical track is formed of: a helical groove which is formed on an inner peripheral surface of the outer cylinder; and a helical slit which is formed in a peripheral wall of the inner cylinder in a penetrating manner corresponding to the helical groove, the syringe holding cylinder has a flange member which is brought into slide contact with the helical groove through the helical slit, and the biasing mechanism is configured to push up the flange member by an elastic body disposed in a space formed between the outer cylinder and the inner cylinder.

Advantages of the Present Invention

According to the aspect of claimed invention, operation steps of removing the injection needle can be simplified and hence, the injection needle removal device can be simplified whereby the injection needle removal device can be used with ease, and a device cost can be also reduced. Further, wastes discarded in the accommodating case are limited to only the injection needle base portions each having the injection needle and hence, a volume of medical wastes can be reduced.

According to the aspect of claimed invention, the turning helical operation of the syringe holding cylinder in the outer cylinder can be performed smoothly performed and hence, a speed of the turning helical operation of the syringe holding cylinder can be accelerated and so that a turning force brought about by a descending operation of the syringe holding cylinder can be increased whereby the injection needle tightening ring can be expanded in a distal-end divided manner with certainty.

According to the aspect of claimed invention, it is possible to prevent an inadvertent removal of the syringe holding cylinder from the outer cylinder, and a turning helical operation of the syringe holding cylinder along the helical track in the outer cylinder can be performed smoothly with certainty while holding a loose fitting state between the helical groove and the projection.

According to the aspect of claimed invention, by effectively making use of a turning force brought about by a turning descending operation of the syringe holding cylinder in the vicinity of the lower locking point, the plurality of divided members are swung outward in a radial direction of the syringe holding cylinder so that the injection needle tightening ring can be expanded in a distal end divided manner whereby it is possible to discard with certainty the injection needle which the injection needle tightening ring holds in the injection needle accommodating case.

According to the aspect of claimed invention, by providing a state where the syringe holding cylinder holds the syringe body more firmly, it is possible to prevent an inadvertent removal of the syringe body from the syringe holding cylinder during an operation of removing the syringe body and hence a removal operation of the injection needle can be performed with certainty.

According to the aspect of claimed invention, the syringe holding cylinder which is disposed at a lower side in the outer cylinder is made to return to an upper side in the outer cylinder, and is held in a standby state at an upper position corresponding to the upper locking point. Accordingly, the syringe can be easily mounted in the syringe holding cylinder.

According to the aspect of claimed invention, the syringe holding cylinder which is disposed at a lower side in the outer cylinder is made to return to an upper side in the outer cylinder more firmly, and is held in a standby state at an upper position corresponding to the upper locking point. Accordingly, the syringe can be easily mounted in the syringe holding cylinder.

DESCRIPTION OF EMBODIMENTS

The present invention relates to a jig for removing an injection needle base portion (connection portion) which is threadedly connected to a distal end of a syringe in a detachable manner by a threadedly removing operation.

<1. Configuration of Syringe>

Figure 17:
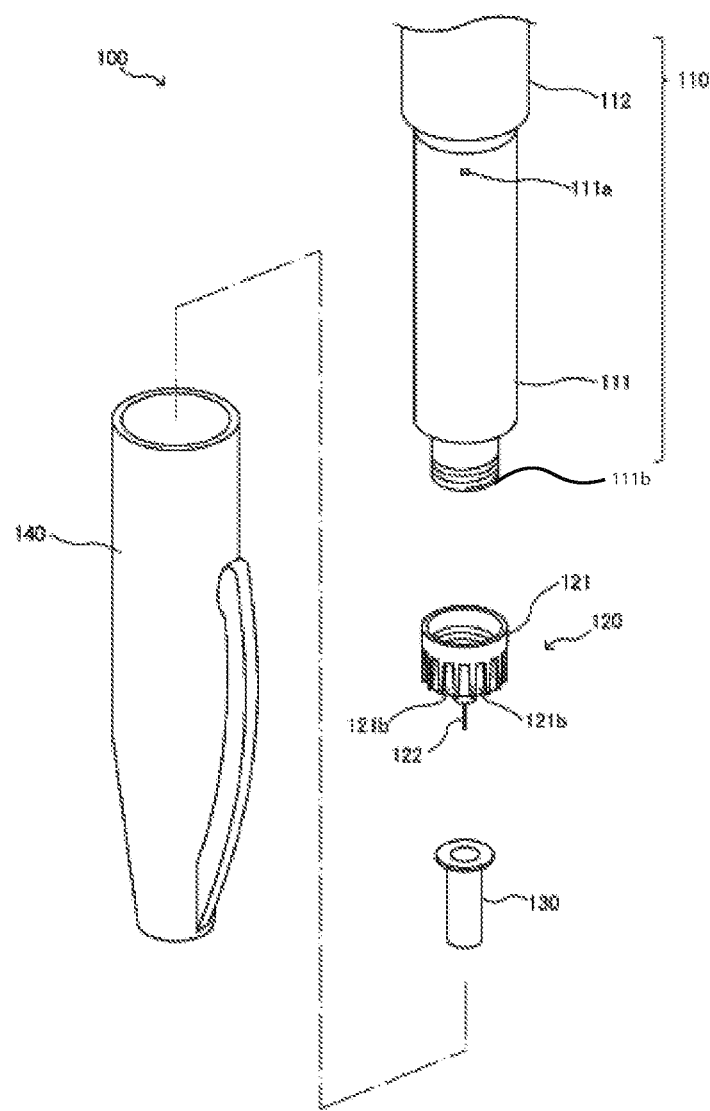
FIG. 17 is an exploded perspective view showing a configuration of a syringe provided for the injection needle removal device according to the present invention.

FIG. 17 is an exploded perspective view showing a configuration of a syringe 100 where an injection needle is removed from a syringe body using an injection needle removal device according to an embodiment of the present invention.

The syringe 100 includes: a syringe body 110 which is formed of a syringe grip portion 112 in which a plunger mechanism for discharging a liquid medicine from an injection needle and the like are accommodated and a cartridge 111 which stores an injection liquid; an injection needle base portion 120 which is threadedly mounted on a distal end of the syringe body 110 (cartridge 111) in a detachable manner; and an injection needle 122 which is mounted on the injection needle base portion 120 in a projecting manner.

As shown in FIG. 17, a male threaded portion 111b is formed on a distal end of the cartridge 111. The injection needle base portion 120 having an injection needle 122 is connected to the distal end of the cartridge 111 in a detachable manner by making a female threaded inner cylinder 121 of the injection needle base portion 120 engage with the male threaded portion 111b.

Further, a plurality of anti-slipping grooves 121b which extends in axial direction are formed on an outer peripheral surface of the female threaded inner cylinder 121 of the injection needle base portion 120 at predetermined intervals. In the injection needle removal device according to the present invention, particularly, the anti-slipping grooves 121b are used as portions for engagement with engaging projections 44 formed on an injection needle tightening ring 21.

In FIG. 17, numeral 130 indicates an injection needle protector which covers the injection needle 122 except when the syringe 100 is used, and numeral 140 indicates a cap which covers the cartridge 111.

In the present invention, by rotating only the injection needle base portion 120 disposed on the distal end of the above-mentioned syringe 100 using the jig, the injection needle base portion 120 is threadedly removed from the distal end of the cartridge 111 together with the injection needle 122. In this manner, the injection needle is automatically or semi-automatically removed and accommodated in an individual container by way of the jig without requiring a direct operation by a human hand. Due to such an operation, it is possible to prevent a pricking accident caused when a removing operation of the injection needle 122 is performed using a hand and fingers after the injection needle 122 is used.

<2. Injection Needle Removal Device According to First Embodiment>

Figure 1:
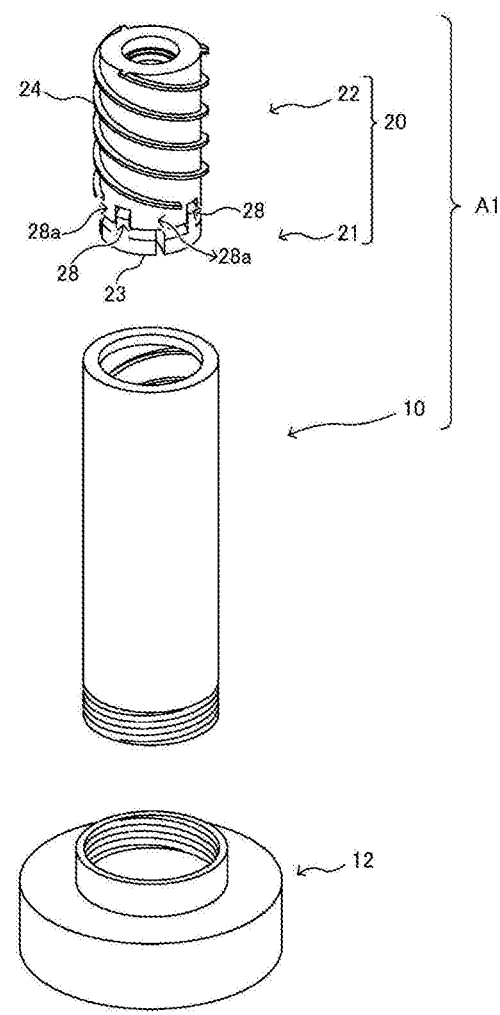
FIG. 1 is an exploded perspective view showing a configuration of an injection needle removal device according to a first embodiment.
Figure 2A:
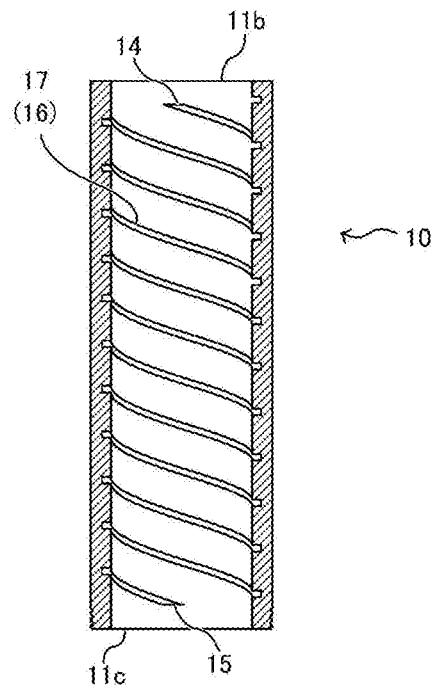
FIG. 2A, 2B are explanatory views showing a configuration of an outer cylinder of the injection needle removal device according to the first embodiment.
Figure 2B:
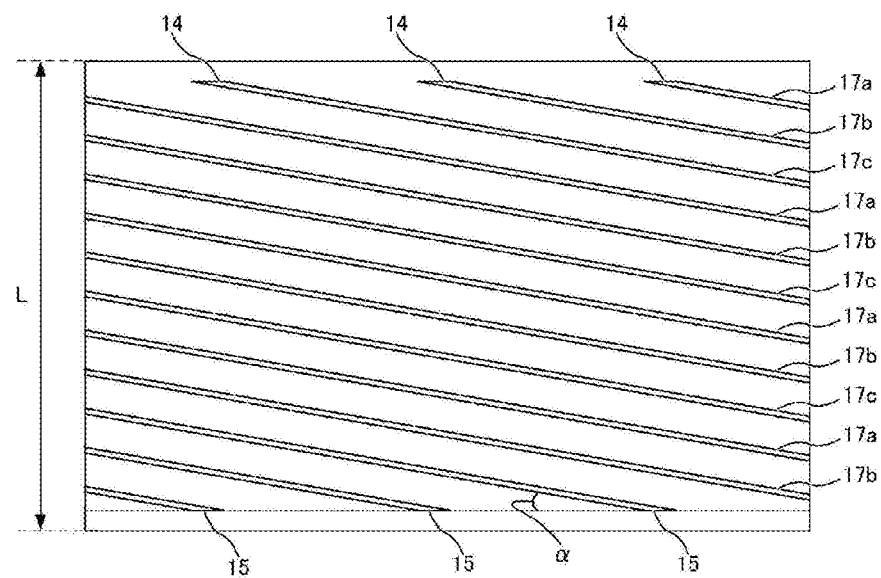

Hereinafter, an injection needle removal device A1 used as a jig for automatically removing the injection needle 122 is described in detail. FIG. 1 is an exploded perspective view of the injection needle removal device. FIG. 2 is a longitudinal cross-sectional view and a developed view of an outer cylinder, FIG. 2A, 2B are longitudinal cross-sectional views of the syringe holding cylinder, FIG. 3A to FIG. 5 are external appearance views of an injection needle tightening ring, FIG. 6 is an explanatory schematic view showing an in-use state of the injection needle removal device, and FIG. 7A to FIG. 8C are longitudinal cross-sectional views showing a step of threadedly removing the injection needle using the injection needle removal device.

The injection needle removal device A1 according to this embodiment is configured such that the injection needle base portion 120 is threadedly removed from the syringe body when a user P sets the cartridge 111 of the syringe 100 and the needle base portion 120 disposed on the distal end of the cartridge 111 on a syringe holding cylinder 20 in the outer cylinder 10 which is fixed to the injection needle accommodation case 30 in an erected manner by way of a case mounting body 12, and the user P performs a pulling-up operation (hereinafter simply referred to as a pull-up-type injection needle removal device).

As shown in FIG. 1, the injection needle removal device A1 includes the syringe holding cylinder 20 and the outer cylinder 10. The syringe holding cylinder 20 is a cylinder where a male threaded portion 24 is formed on an outer peripheral surface as a helical groove. The outer cylinder 10 is a cylinder where a female threaded portion 17 is formed on an inner peripheral surface as a helical ridge.

As shown in FIG. 2A, the outer cylinder 10 is formed such that an upper opening of the outer cylinder 10 is formed as a syringe insertion opening 11b and a lower opening of the outer cylinder 10 is formed as an ejection opening 11c for ejecting the injection needle base portion 120. A lower end portion of the outer cylinder 10 is threadedly mountable on the case mounting body 12 which is mounted on an upper opening of the injection needle accommodation case 30 as shown in FIG. 1 and FIG. 6.

Figure 3A:
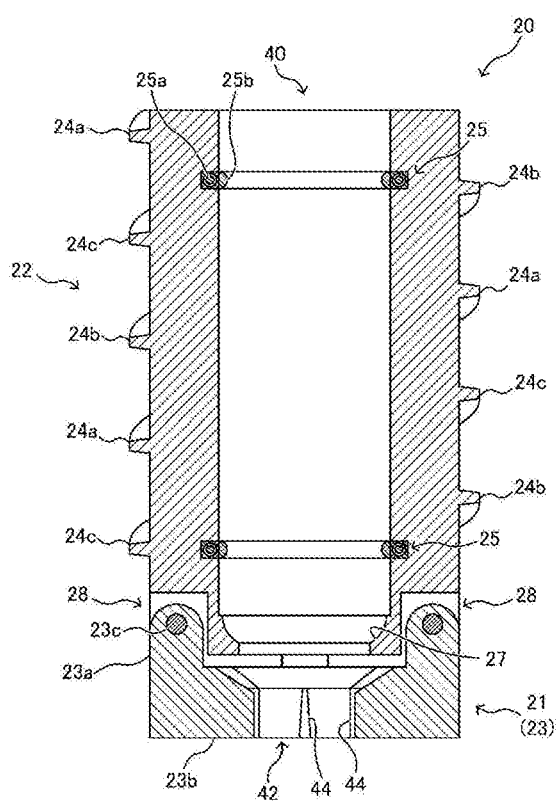
FIG. 3A, 3B are cross-sectional views showing a configuration of a syringe holding cylinder of the injection needle removal device according to the first embodiment.

As shown in FIG. 3A, the syringe holding cylinder 20 includes: a syringe holding cylinder body 22 which is formed such that the syringe body 110 is insertable in the syringe holding cylinder body 22; and an injection needle tightening ring 21 which is disposed at an lower end of the syringe holding cylinder body 22 such that the injection needle base portion 120 on the distal end of the syringe body 110 can be fitted in the injection needle tightening ring 21. An inner space of the syringe holding cylinder 20 forms a fitting mounting hole 40, and the syringe body 110 (cartridge 111) of the syringe 100 and the injection needle base portion 120 are inserted and fitted in the fitting mounting hole 40.

An O-ring 25b is mounted on an inner wall of the syringe holding cylinder 20 (syringe holding cylinder body 22) at predetermined positions as grip means 25. The O-rings 25b are provided for holding tightness between the syringe 100 and the outer peripheral surface of the syringe body 110 when the syringe 100 is inserted into the syringe holding cylinder 20.

It is sufficient for the grip means 25 to be formed such that the syringe holding cylinder 20 tightly grips the syringe body 110 by generating a high friction force against a stress in an axial direction of the outer cylinder 10, while the grip means 25 allow the syringe body 110 and the syringe holding cylinder 20 to slide relative to each other in a rotational direction (circumferential direction) of the syringe holding cylinder 20.

Figure 3B:
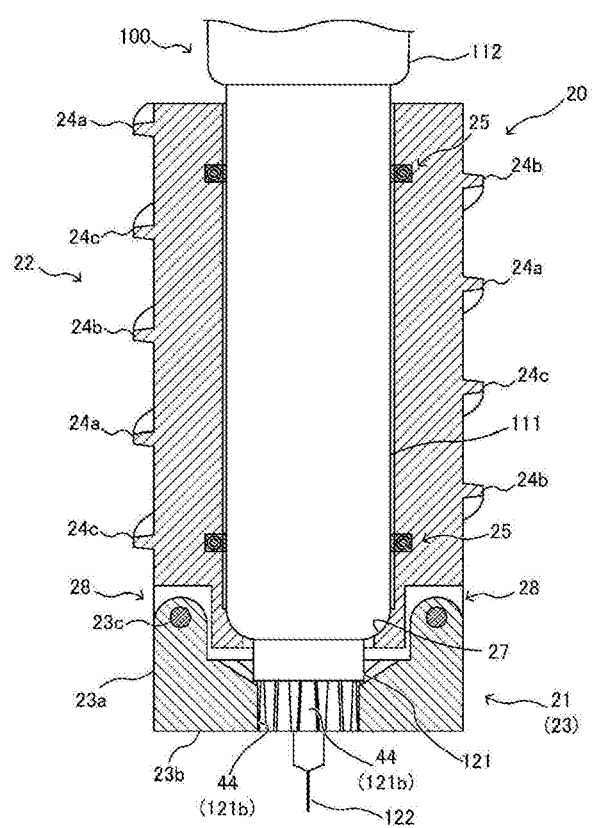

Particularly, as shown in FIG. 3A, 3B, each grip means 25 of this embodiment has a bearing structure which is formed of: a bearing 25a formed of two (inner and outer) rings disposed on the same axis with rolling bodies interposed therebetween; and the O-ring 25b which is mounted on an inner peripheral wall of the bearing 25a. Such a bearing structure is provided to two (upper and lower) portions of the inner peripheral wall of the syringe holding cylinder body 22.

Due to such a bearing structure, the inner ring idles by way of the rolling bodies with respect to turning rotation of the syringe holding cylinder body 22 brought about by ascending or descending of the syringe holding cylinder 20. Accordingly, there is no possibility that such a turning rotational force is transmitted to the syringe body 110 (cartridge 111) so that a fixed state of the syringe body 110 brought about by gripping of the syringe body 110 by a hand of the user can be ensured, and the turning rotational force is transmitted only to the injection needle base portion 120.

Further, an engaging stepped portion 27 which projects inward in a radial direction of the syringe holding cylinder body 22 is formed on a lowermost edge of an inner wall of the syringe holding cylinder body 22 such that the engaging stepped portion 27 is brought into contact and engages with a front edge of the cartridge 111. With such a configuration, when the syringe body 110 is inserted into the syringe holding cylinder body 22, the injection needle base portion 120 disposed on the distal end of the syringe body 110 can be positioned at the injection needle tightening ring 21 of the syringe holding cylinder 20.

As shown in FIG. 1, four cutout portions 28 are formed on a thick peripheral wall of a lower end portion of the syringe holding cylinder 20 (syringe holding cylinder body 22) at an interval of approximately 90°. Four semicircular-arc-shaped support wall bodies 28a are formed such that each support wall body 28a is interposed between each two of four cutout portions 28 respectively. The injection needle tightening ring 21 described later is connected to these cutout portions 28 and support wall bodies 28a in an expandable and openable manner.

As shown in FIG. 2B, the openable and closeable injection needle tightening ring 21 has a short cylindrical shape, and the inside of the injection needle tightening ring 21 forms a needle fitting mounting hole 42 in which the injection needle base portion 120 is mounted by fitting. An inner diameter of the needle fitting mounting hole 42 is set substantially equal to an outer diameter of the female threaded inner cylinder 121.

As shown in FIG. 3A to FIG. 5, the injection needle tightening ring 21 is formed of four divided members 23, and each divided member 23 includes: a ring-use support projection 23a and a ring-use spacer portion 23b. Four ring-use support projections 23a engage with four cutout portions 28 and four support wall bodies 28a of the syringe holding cylinder 20 alternately by fitting engagement, and each of four ring-use spacer portions 23b is formed between each two of four support wall bodies 28a respectively.

The divided members 23 are arcuate pieces formed by dividing a circular cylinder which forms the injection needle tightening ring 21 about an axis of the circular cylinder at a predetermined interval. In this embodiment, the circular cylinder is formed of four divided arcuate pieces which are obtained by dividing the circular cylinder in four. It is preferable that the number of divided members 23 be set to two to six.

As shown in FIG. 3A, the divided member 23 has an approximately L shape as viewed in transverse cross section. A vertically extending portion of the L-shaped divided member 23 forms a ring-use support projection 23a, and a horizontal portion of the L-shaped divided member 23 forms a ring-use spacer portion 23b. The ring-use spacer portion 23b has a thickness larger than a thickness of the ring-use support projection 23a and extends along a circumference of the injection needle base portion 120.

Figure 4A:
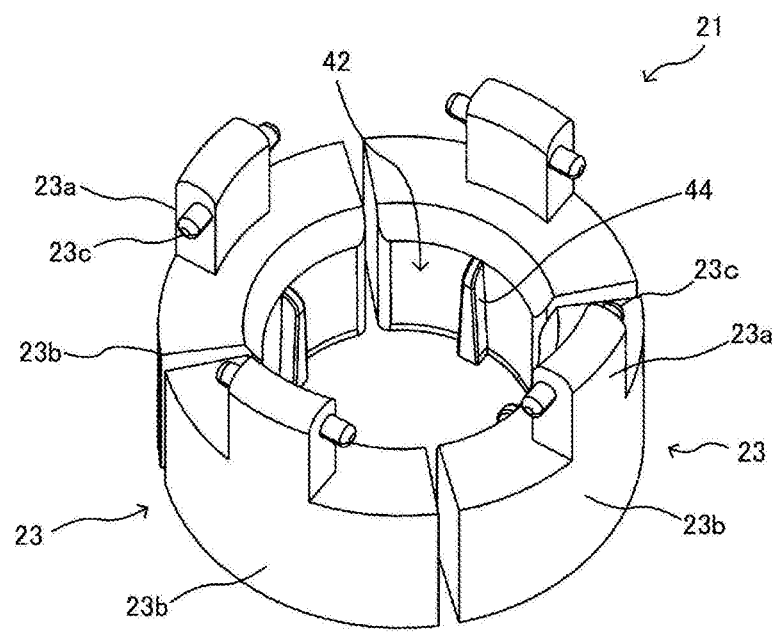
FIG. 4A, 4B are explanatory views showing a configuration of an injection needle tightening ring of the injection needle removal device according to the first embodiment.
Figure 4B:
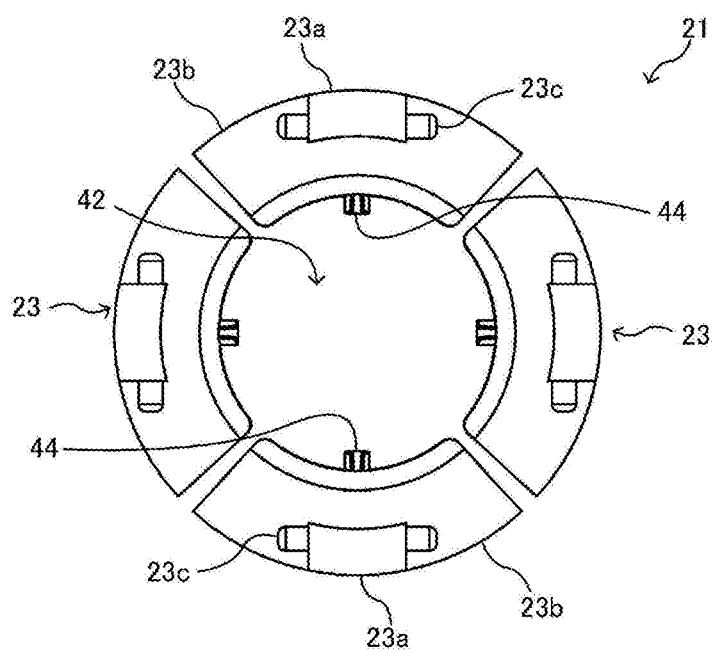
Figure 5:
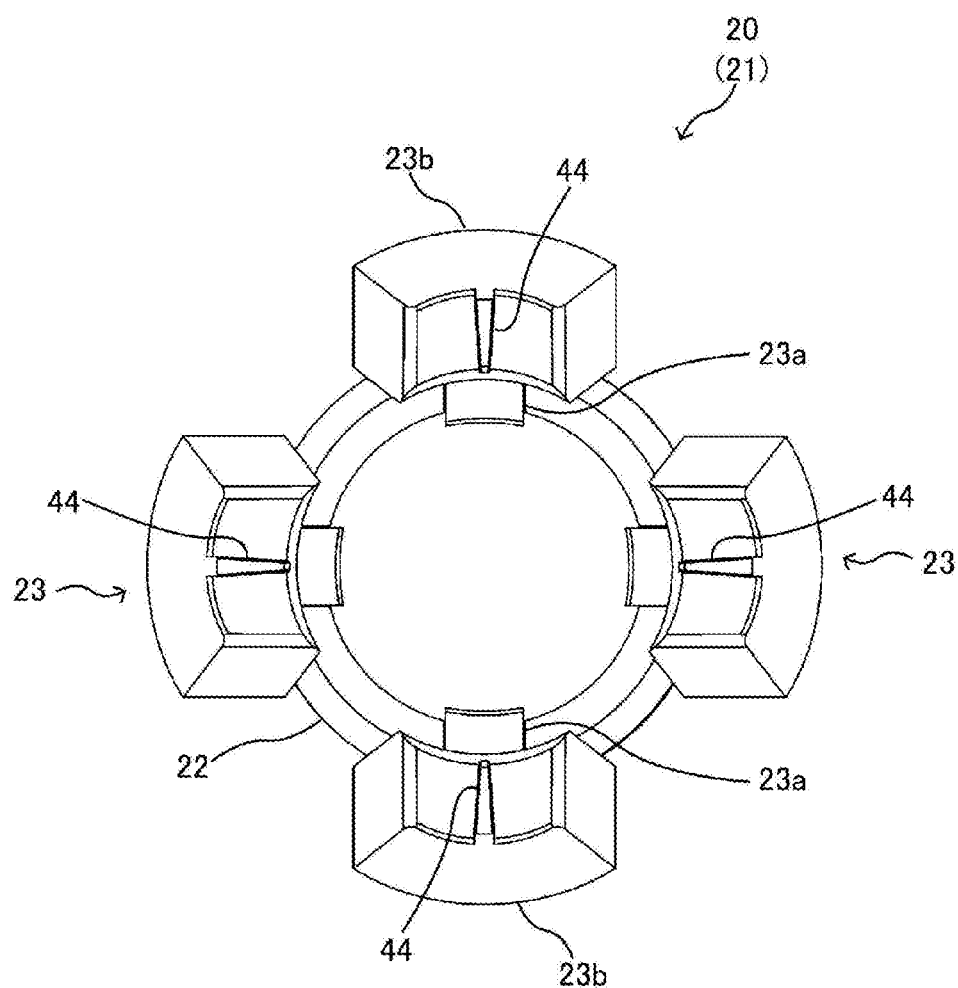
FIG. 5 is an explanatory view showing a configuration of the injection needle tightening ring of the injection needle removal device according to the first embodiment.
Figure 6:
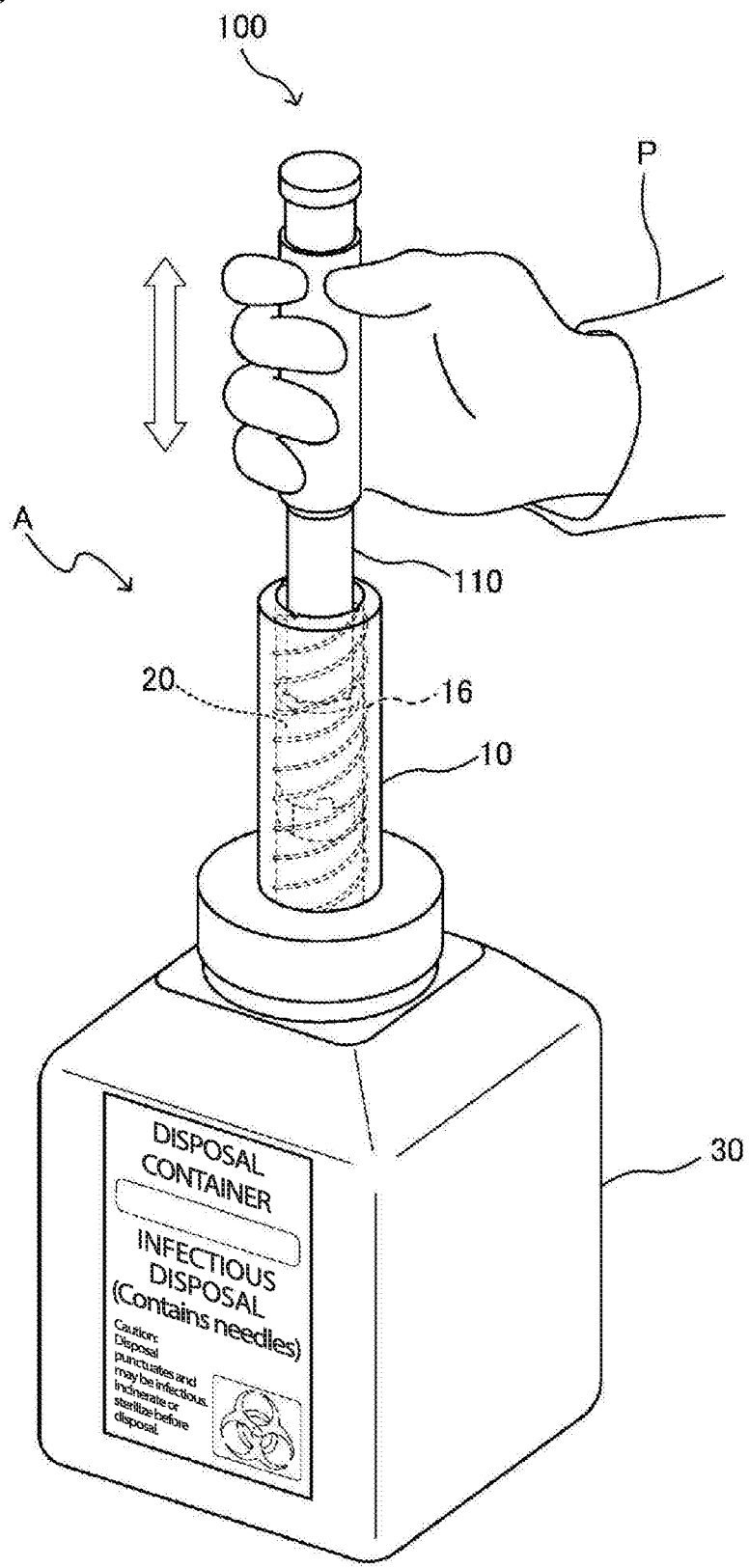
FIG. 6 is a schematic explanatory view showing an in-use state of the injection needle removal device according to the present invention.

As shown in FIG. 4A to FIG. 5, the cutout portions 28 and the support wall bodies 28 which are formed on the lower end portion of the syringe holding cylinder 20 alternately engage with the ring-use support projections 23a and the ring-use spacer portions 23b of the separately-prepared injection needle tightening ring 21 respectively by fitting engagement.

Further, the lower end portion of the syringe holding cylinder 20 and the injection needle tightening ring 21 are connected to each other as follows. That is, the ring-use support projection 23a of the injection needle tightening ring 21 and the support wall bodies 28a between which the ring-use spacer portion 23b is loosely fitted are respectively pivotally connected to each other by way of pivot shafts 23c which project from both side ends of the ring-use support projection 23a.

As shown in FIG. 4B, with respect to the ring-use support projection 23a, the position of the pivot shaft 23c is set at an outwardly offset position such that the center of gravity of a lower portion of the ring-use support projection 23a is displaced outward so that the ring-use support projections 23a can be expanded outward in a free state.

In this manner, the injection needle tightening ring 21 which is connected to the lower end portion of the syringe holding cylinder 20 is configured such that, in a free state (a state where the lower end of the syringe holding cylinder 20 projects from the lower end portion of the outer cylinder 10), as shown in FIG. 5, the divided members 23 can be expanded outward about the pivot shafts 23c of the ring-use support projections 23a.

Further, as shown in FIG. 3A to FIG. 5, on inner peripheral wall surfaces of the respective four divided members 23 which are formed by dividing the injection needle tightening ring 21 in four, a plurality of engaging projections 44 which are brought into contact and engage with an outer peripheral surface of the injection needle base portion 120, that is, the anti-slipping grooves 121b are formed in a projecting manner.

The engaging projections 44 are engageable with the outer peripheral surface of the injection needle base portion 120. That is, in threadedly inserting the syringe holding cylinder 20 into the outer cylinder 10, as shown in FIG. 4B, the syringe 100 is inserted into the syringe holding cylinder 20 in advance, and the engaging projections 44 on the inner peripheral wall of the divided members 23 of the injection needle tightening ring 21 are brought into contact and engaged with the outer peripheral surface of the injection needle base portion 120.

The female threaded portion 17 which forms a helical groove is formed on the inner peripheral wall surface of the outer cylinder 10. As shown in FIG. 7A to FIG. 8C, the female threaded portion 17 threadedly engage with the male threaded portion 24 which is formed as a helical ridge on the inner peripheral surface of the syringe holding cylinder 20.

As shown in FIG. 2A, 2B, the female threaded portion 17 is formed as a helical track 16 on the inner peripheral surface of the outer cylinder 10 from an upper locking point 14 to a lower locking point 15.

In other words, a helical groove is formed as the helical track 16 on the inner peripheral surface of the outer cylinder 10, the upper locking point 14 of the helical track 16 forms an upper closing end of the helical groove at an upper inner peripheral edge portion of the outer cylinder 10, and the lower locking point 15 of the helical track 16 forms a lower closing end of the helical groove at a lower inner peripheral edge portion of the outer cylinder 10.

On the other hand, as shown in FIG. 3A, 3B, on an outer peripheral surface of the syringe holding cylinder 20 (syringe holding cylinder body 22), the male threaded portion 24 which threadedly engage with the female threaded portion 17 of the outer cylinder 10 is formed in a projecting manner.

In other words, the helical ridge which can be brought into slide contact with the helical groove is formed on the outer peripheral surface of the syringe holding cylinder 20 corresponding to the helical groove which is the helical track 16 formed on the inner peripheral surface of the outer cylinder 10.

The upper locking point 14 and the lower locking point 15 on both ends of the female threaded portion 17 of the outer cylinder 10 respectively function as a stopper which define terminals of the threadedly advancing or retracting movement of the syringe holding cylinder 20.

As an idea, it is also considered that a width of the female threaded portion 17 of the outer cylinder 10 is set slightly larger than a width of the male threaded portion 24 of the syringe holding cylinder 20, locking projecting portions which form the upper locking point 14 and the lower locking point 15 corresponding to the desired locking positions of the syringe holding cylinder 20 are formed on intermediate portions of the female threaded portion 17 respectively, and locking stepped portions are formed on intermediate portions of the female threaded portion 24 of the syringe holding cylinder 20 in a projecting manner in a corresponding manner with the locking projecting portions.

That is, by providing the upper locking point 14 and the lower locking point 15 to the intermediate portions of the helical track 16 (female threaded portion 17) or by providing the upper locking point 14 and the lower locking point 15 additionally, the both ends of the female threaded portion 17 are formed as open ends. In this case, an upper portion and a lower portion of the syringe holding cylinder 20 which threadedly advance and retract in the outer cylinder 10 from above or below the outer cylinder 10 can be made extensible or retractable.

The helical directions of the female threaded portion 17 and the male threaded portion 24 become equal to the helical direction that the injection needle base portion 120 is threadedly removed from the syringe body 110 when the syringe holding cylinder 20 performs a turning and ascending movement.

A helical length of the female threaded portion 17 of the outer cylinder 10 is set to a helical length which can ensure the number of turns which allow the injection needle base portion 120 to be threadedly removed from the syringe body 110 during the movement of the syringe holding cylinder 20 in the outer cylinder 10 which reaches the lower locking point 15 from the upper locking point 14. In this embodiment, the helical length of the female threaded portion 17 is set to a helical length which allows the syringe holding cylinder 20 in the outer cylinder 10 to turn at least three times.

That is, by making a helical length between the upper locking point 14 and the lower locking point 15 correspond to a helical turning distance necessary for threadedly removing the injection needle base portion 120, when the syringe holding cylinder 20 in the outer cylinder 10 reaches a helical terminal point, an operation of threaded removing the injection needle base portion 120 is finished so that a separation and removal operation of the injection needle base portion 120 is finished.

As shown in FIG. 2B, a lead angle $\alpha$ of the male threaded portion 17 is set to a lead angle which allows the syringe holding cylinder 20 in the outer cylinder 10 to turn and descend due to the own weight of the syringe holding cylinder 20. A height L of the outer cylinder 10 on which the female threaded portion 17 having such a lead angle $\alpha$ and such a length is set to a height which allows the user P to perform a separation and removal operation of the injection needle base portion 120 in a state where the user P grasps the syringe body 110.

The injection needle removal device A1 has the multiple threads structure formed of the above-mentioned male threaded portion 24 and female threaded portion 17.

That is, as shown in FIG. 2B, the multiple threads structure is configured such that a first female threaded portion 17a, a second female threaded portion 17b, and a third female threaded portion 17c are formed on the inner peripheral surface of the outer cylinder 10 at the same lead angle $\alpha$ and at the same predetermined pitch. Further, corresponding to these first to third female threaded portions 17a to 17c, a first male threaded portion 24a, a second male threaded portion 24b, and a third male threaded portion 24c are formed on the outer peripheral surface of the syringe holding cylinder 20 (syringe holding cylinder body 22) in a projecting manner.

Due to such a multiple threads structure, while ensuring a large lead angle $\alpha$, a contact area in threadedly engaging the outer cylinder 10 and the syringe holding cylinder 20 with each other at helical portions formed on oppositely facing surfaces of the outer cylinder 10 and syringe holding cylinder 20a can be increased so that a pressing force for pressing the outer cylinder 10 downward in the axial direction can be dispersed. The number of helical tracks 16 which form the multiple threads structure can be set to two to four, for example.

It is needless to say that, contrary to this embodiment, the threaded structure can be also formed such that a male threaded portion (a helical ridge) is formed on the inner peripheral surface of the outer cylinder 10 and a female threaded portion (helical groove) is formed on the outer peripheral surface of the syringe holding cylinder 20 corresponding to the male threaded portion.

Figure 7A:
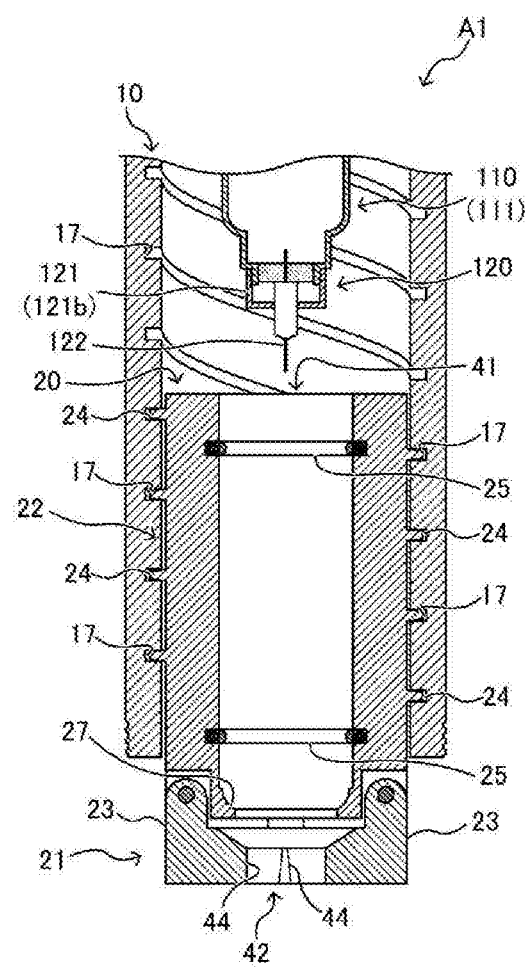
FIG. 7A, 7B, 7C are explanatory views showing a step of threadedly removing an injection needle by the injection needle removal device according to the first embodiment.
Figure 7B:
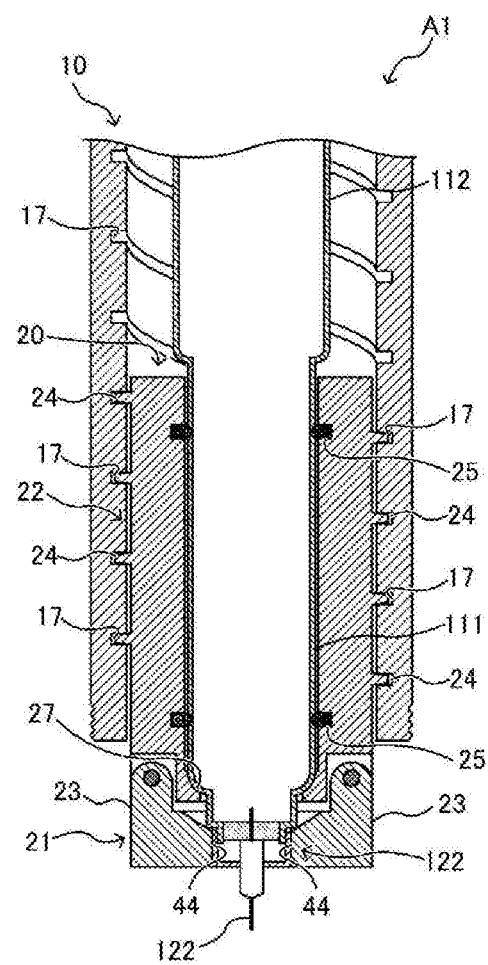
Figure 7C:
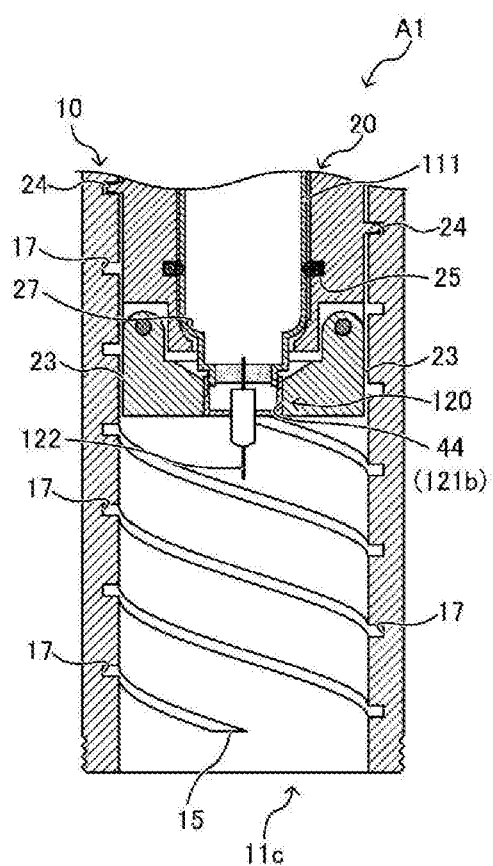
Figure 8A:
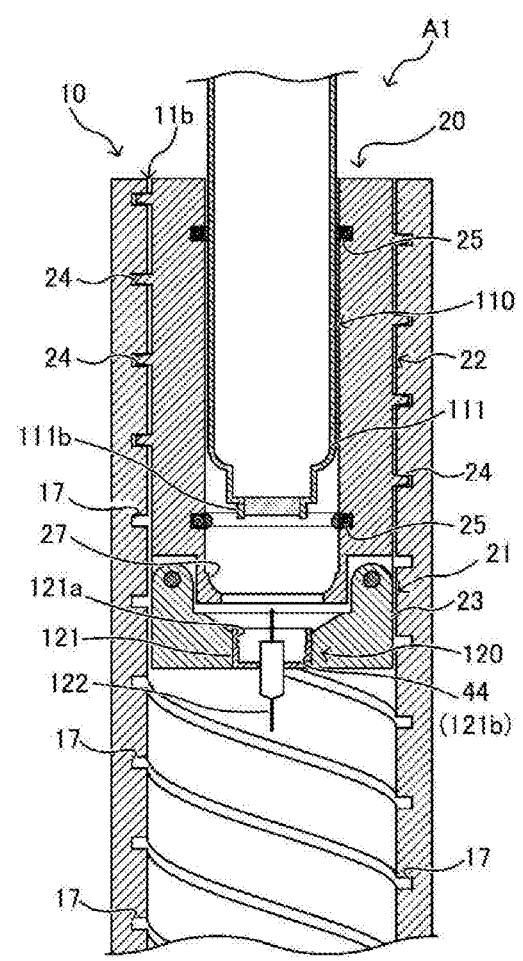
FIG. 8A, 8B, 8C are explanatory views showing a step of threadedly removing the injection needle by the injection needle removal device according to the first embodiment.
Figure 8B:
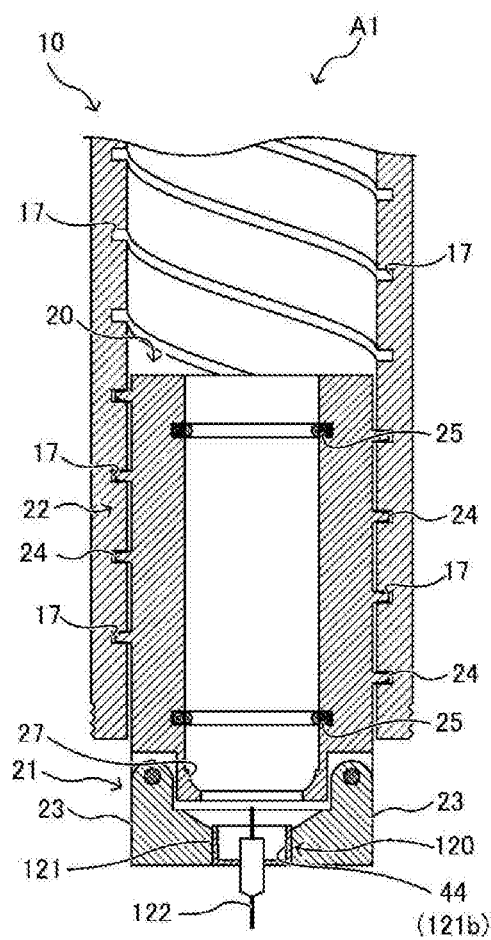
Figure 8C:
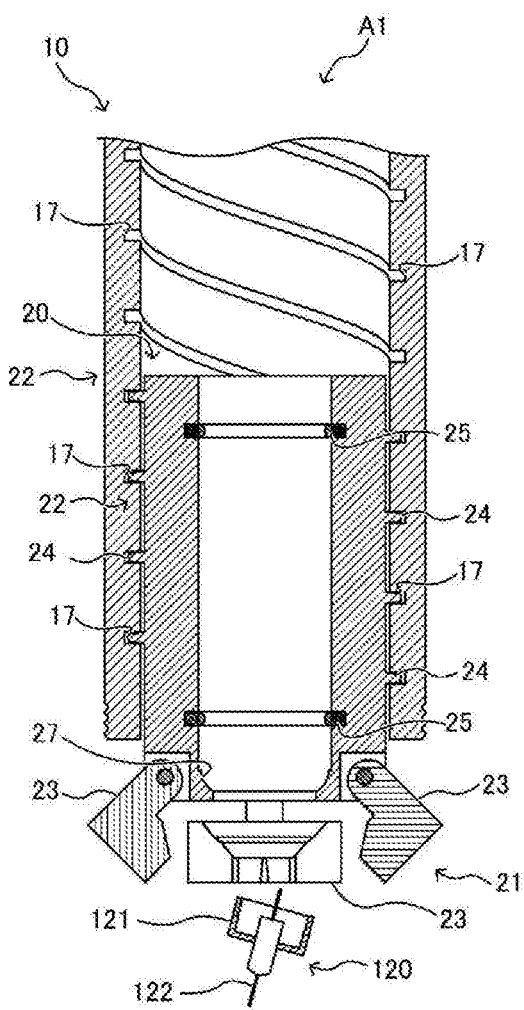

In threadedly inserting the syringe holding cylinder 20 in a state where the syringe holding cylinder 20 holds the syringe 100 in the syringe holding cylinder 20 into the outer cylinder 10, in the outer cylinder 10, as shown in FIG. 7C and FIG. 8A, the divided members 23 of the injection needle tightening ring 21 formed on the lower end of the syringe holding cylinder 20 are restricted by the inner peripheral wall surface of the outer cylinder 10 so that the divided members 23 are in an expansion prevention state. When the syringe holding cylinder 20 further advances helically, as shown in FIG. 8B and FIG. 8C, the divided members 23 of the syringe holding cylinder 20 project from the lower end of the outer cylinder 10 so that the divided members 23 are brought into an exposed state.

In such a state, the divided members 23 of the injection needle tightening ring 21 are released from the restriction imposed on the divided members 23 by the outer cylinder, and are brought into a free state. Accordingly, an offset load is applied to the divided member 23 in an expansion direction about the pivot shaft 23c of the ring-use support projection 23a so that a release state is brought about where the divided member 23 expand.

At this stage of the operation, as described above, the injection needle base portion 120 is brought into a state where the injection needle base portion 12 is threadedly removed from the cartridge 111 in the outer cylinder 10 and in a separated state. Further, when the restriction and holding of the injection needle base portion 120 by the outer periphery of the divided member 23 are eliminated, the injection needle base portion 120 is released along with the expansion of the divided members 23 and automatically falls downward from between the divided members 23, and falls and is accommodated in the injection needle accommodation case.

Hereinafter, an in-use example of the injection needle removal device A1 is described in detail. In an unused state of the injection needle removal device A1, as shown in FIG. 7A, the syringe holding cylinder 20 is stopped in a state where the injection needle tightening ring 21 is exposed downward from the ejection opening 11c of the outer cylinder 10 at the lower locking point 15 in the outer cylinder 10, and the plurality of divided members 23 which form the injection needle tightening ring 21 are brought into a free state in a radially outward direction of the syringe holding cylinder 20 respectively.

With respect to the injection needle removal device A1 in such a state, a user P presses the syringe body 110 into the fitting mounting hole 40c of the syringe holding cylinder 20 until the injection needle base portion 120 is positioned at the injection needle tightening ring 21 which is exposed downward from the ejection opening 11c of the outer cylinder 10, and sets the syringe 100 to the injection needle removal device A1.

That is, as shown in FIG. 7B, the user P pushes the syringe body 110 against a friction force of the grip means 25 until the distal end edge of the cartridge 111 impinges on the engaging stepped portion 27 of the syringe holding cylinder body 22, and positions the injection needle base portion 120 at the position of the injection needle tightening ring 21 which is exposed from the outer cylinder 10 on the lower side of the outer cylinder 10.

In this manner, in the injection needle removal device A1, the cartridge 111 of the syringe body 110 is tightly gripped by the grip means 25 in the syringe holding cylinder body 22 and, at the same time, the ring-use spacer portions 23b of the plurality of divided members 23 which form the injection needle tightening ring 21 are disposed around the outer periphery of the female threaded inner cylinder 121 of the injection needle base portion 120.

Next, along with the pulling-up operation of the syringe body 110 performed by the user P, the syringe holding cylinder 20 starts a turning and ascending movement thus pulling up the exposed injection needle tightening ring 21 into the outer cylinder 10.

Along with such an operation, the outer peripheral surfaces of the respective divided members 23 in a free state are supported by the inner peripheral wall portion of the outer cylinder 10 from the outside, and the divided members 23 are gathered with each other in a bud shape thus forming the circular cylindrical injection needle tightening ring 21 having the needle fitting mounting hole 42 in the inside of the injection needle tightening ring 21.

At this stage of the operation, the ring-use spacer portions 23b of the plurality of divided members 23 move toward the center of axis so as to surround the whole region of the outer peripheral side of the injection needle base portion 120 from the outside, and the engaging projections 44 of the injection needle tightening ring 21 are fitted into the anti-slipping grooves 121b of the injection needle base portion 120 so that the fitting state of the injection needle base portion 120 into the needle fitting mounting hole 42 is completed, and the movement of the injection needle base portion 120 is restricted.

When the pulling-up operation of the syringe body 110 is further performed in such a state, as shown in FIG. 7C, the syringe holding cylinder 20 performs the turning and ascending movement in the outer cylinder 10 along the female threaded portion 17 in a state where the syringe holding cylinder 20 is fitted with the injection needle base portion 120, and the injection needle base portion 120 which is held by being clamped by the injection needle tightening ring 21 is gripped by the user's hand and is rotated in a releasing diction with respect to the syringe body 110 which is in a non-movable state in a rotational direction. Accordingly, the injection needle base portion 120 starts to be gradually removed from the syringe body 110 and, finally, the injection needle base portion 120 is completely threadedly removed from the syringe body 110 as shown in FIG. 8A.

After the syringe body 110 is removed from the syringe holding cylinder body 22 against a friction force of the grip means 25, the syringe holding cylinder 20 performs helical descending movement along the helical track 16 in the outer cylinder 10 due to the syringe holding cylinder 20 together with the weight of the injection needle base portion 120 which is fitted in the syringe holding cylinder 20.

That is, as shown in FIG. 8B, the syringe holding cylinder 20 is locked or stopped by impinging on the lower locking point 15 of the outer cylinder 10, and the respective divided members 23 are swung outward and are brought into an expanded state due to such a stopping reaction of the syringe holding cylinder 20 as shown in FIG. 6 and FIG. 8C so that the injection needle base portion 120 is discarded in the injection needle accommodation casing 30.

The injection needle removal device A1 according to this embodiment is configured as a so-called pull-up-type injection needle removal device where, in the helical track 16 of the outer cylinder 10, a turning and ascending forward path of the syringe holding cylinder 20 is used as a path for threadedly removing the injection needle base portion 120 from the syringe body 110, and a turning and descending return path of the syringe holding cylinder 20 is used as a path for discarding the injection needle base portion 120 into the injection needle accommodation case 30.

That is, in the turning and ascending forward path of the syringe holding cylinder 20, a turning stress which is generated by the pull-up operation by the user P can be used as a rotational force for removing the injection needle base portion 120 from the syringe body 110. In the turning and descending return path of the syringe holding cylinder 20, a turning stress generated by self-weight descending of the syringe holding cylinder 20 can be used as a rotational force which is a force for expanding the injection needle tightening ring 21 in a front-side divided shape so as to discard the injection needle base portion 120 separated and removed from the injection needle tightening ring 21 into the injection needle accommodation case 30.

[4. Injection Needle Removal Device According to Second Embodiment]

Figure 9:
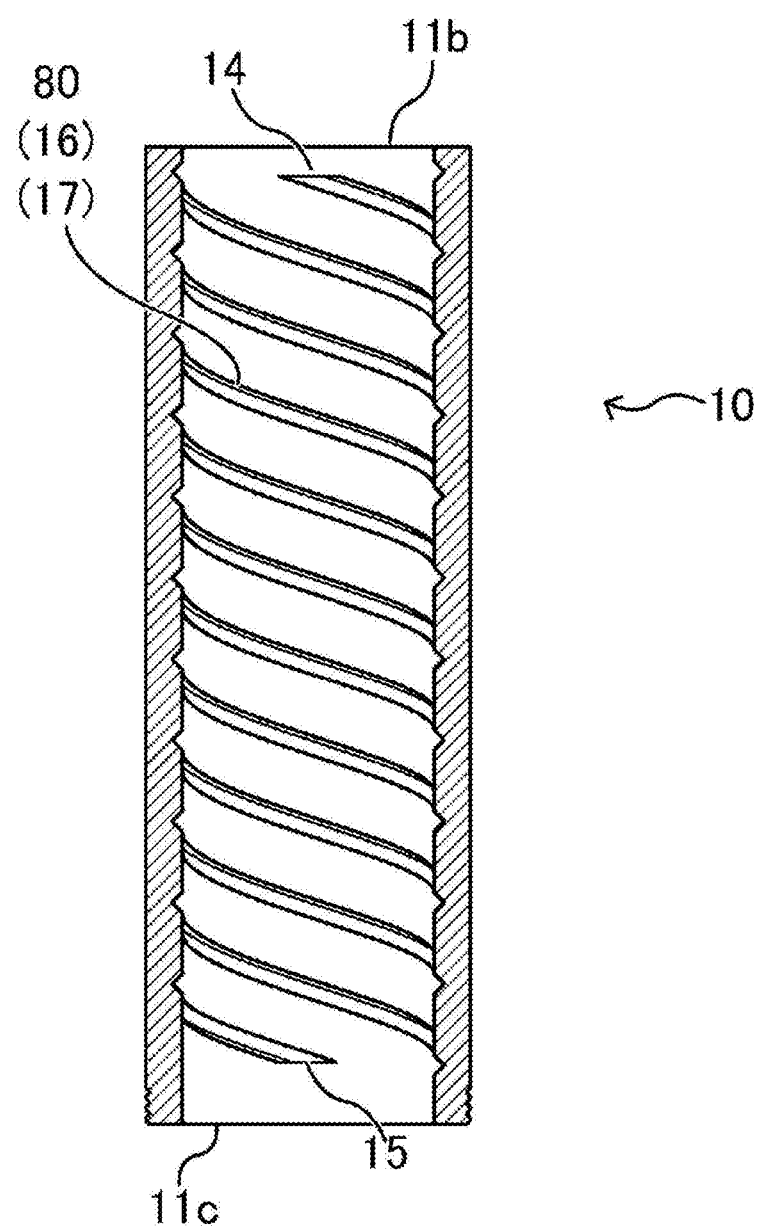
FIG. 9 is an explanatory view showing an internal configuration of an outer cylinder of an injection needle removal device according to a second embodiment.
Figure 10A:
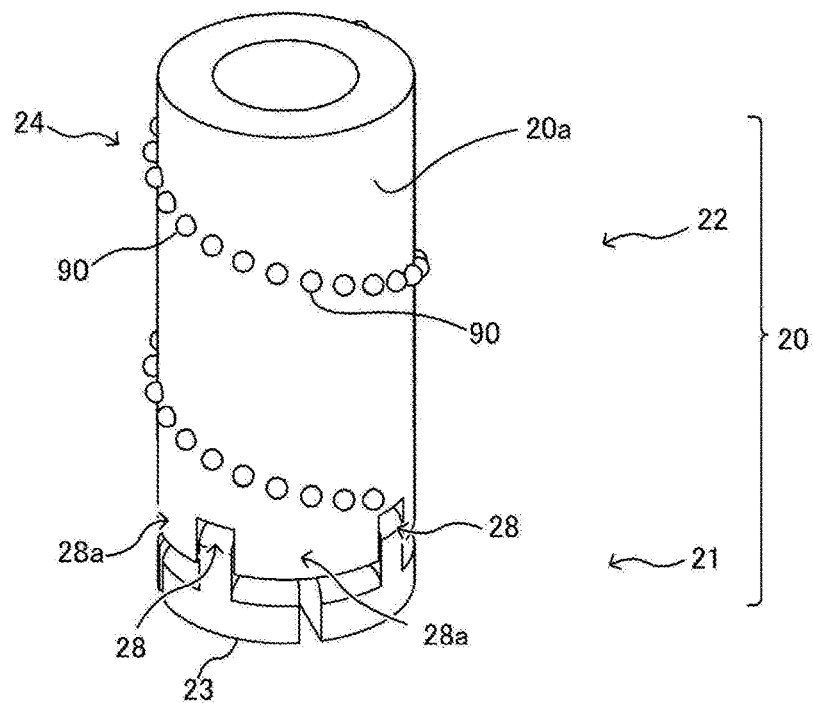
FIG. 10A, 10B are external appearance perspective views showing a configuration of a syringe holding cylinder of the injection needle removal device according to the second embodiment.
Figure 10B:
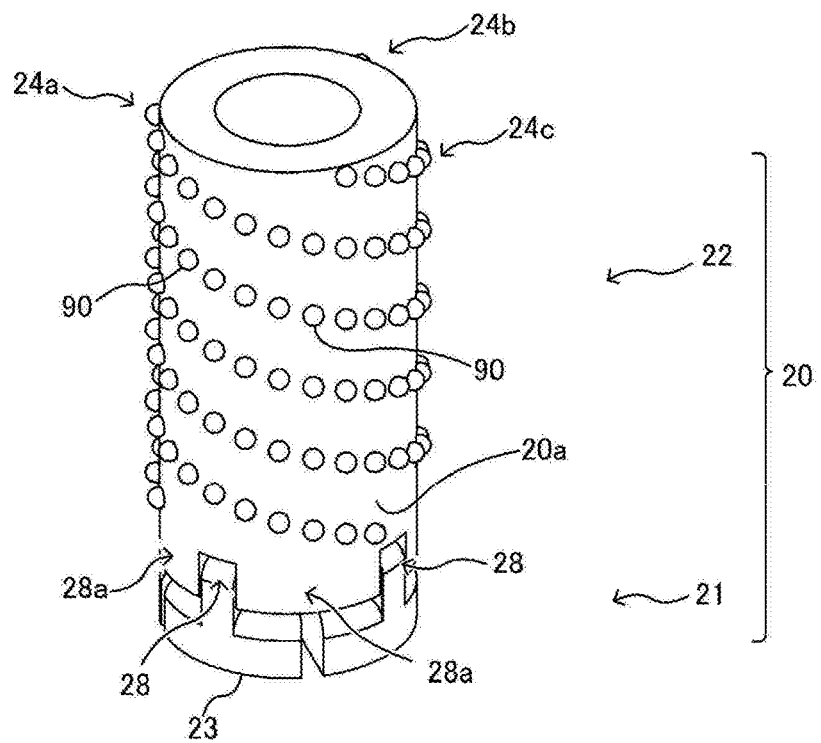
Figure 11A:
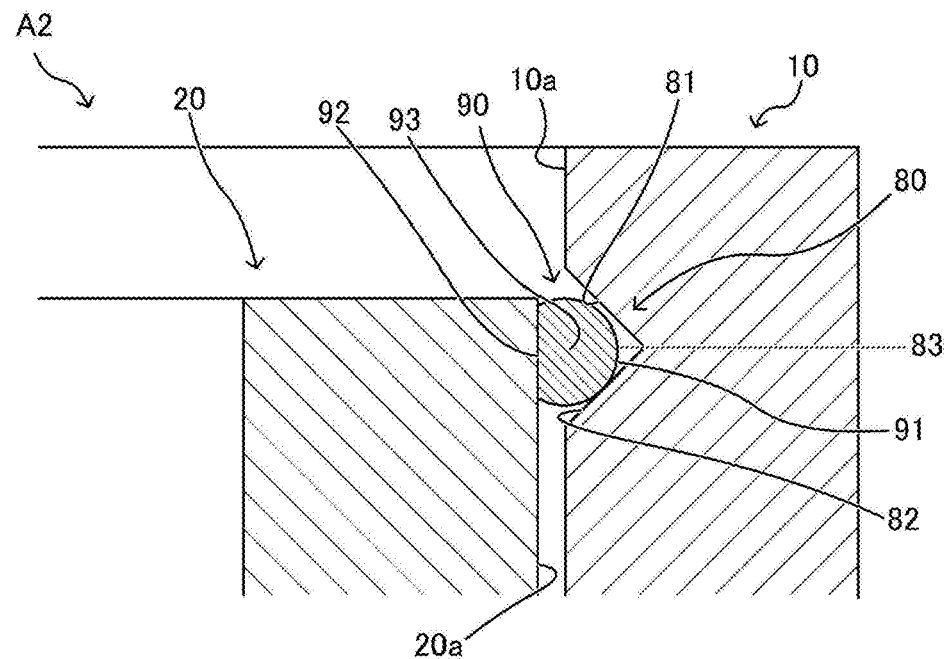
FIG. 11A, 11B are cross-sectional views showing a loose-fitting state between a helical groove of the outer cylinder of the injection needle removal device and a protrusion of a syringe holding cylinder according to the second embodiment.
Figure 11B:
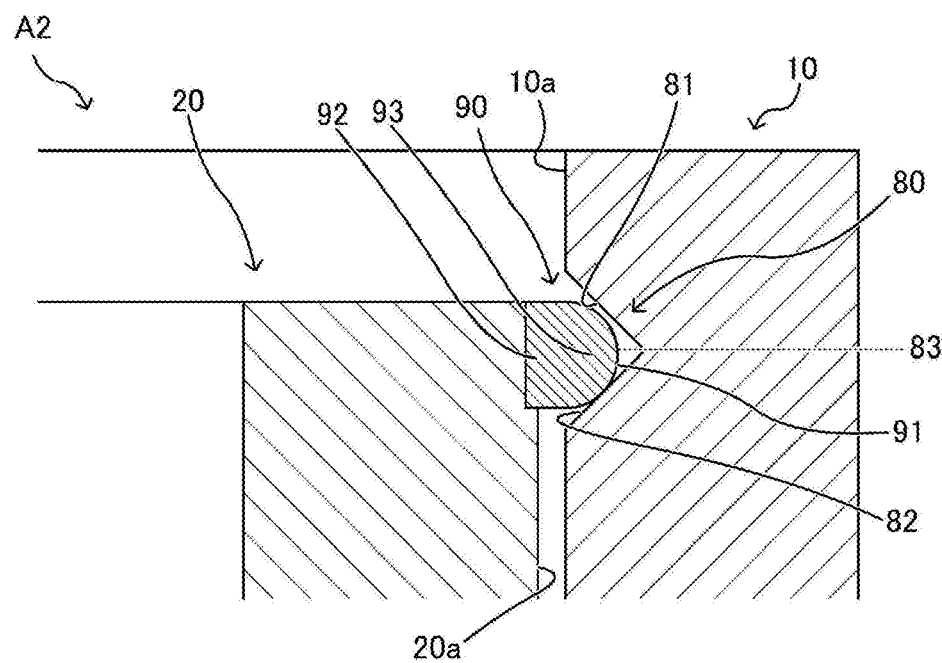

Next, an injection needle removal device according to a second embodiment is described in detail. FIG. 9 is a longitudinal cross-sectional view of an outer cylinder, FIG. 10A, 10B are external appearance perspective views of a syringe holding cylinder, and FIG. 11A, 11B are cross-sectional views showing a loose fitting state between a helical groove of the outer cylinder and a projection of an injection needle holder.

In the injection needle removal device A2 according to this embodiment, the turning and helical advancing of the syringe holding cylinder 20 is realized by bringing projections 90 which are formed on an outer peripheral surface 20a of the syringe holding cylinder 20 (syringe holding cylinder body 22) into slide contact with a helical groove 80 which forms a helical track 16 formed on an inner peripheral surface 10a of the outer cylinder 10 as shown in FIG. 9 to FIG. 11B.

That is, as shown in FIG. 9 to FIG. 11B, an injection needle removal device A3 is configured such that while upper and lower tapered surfaces 81, 82 which expand inward in a radial direction of the outer cylinder 10 are formed on the helical groove 80, each projection 90 is formed in a semispherical shape having a circular arcuate surface on a distal end thereof, and the projections 90 are brought into point contact with the tapered surfaces 81, 82 and hence, a sliding resistance generated between the helical groove 80 and the projections 90 at the time of turning and helical advancing the syringe holding cylinder 20 can be reduced.

The helical groove 80 functions as the above-mentioned female threaded portion 17 and extends along the helical track 16 on the inner peripheral surface of the outer cylinder 10. The helical groove 80 is a tapered groove which is formed by cutting an inner wall of the outer cylinder 10 so as to expand cut surfaces formed on the inner wall inwardly in the radial direction of the outer cylinder 10 in an inverse triangular shape as viewed in cross section.

As shown in FIG. 11A, the helical groove 80 has the upper tapered surface 81 which is positioned on an upper side and the lower tapered surface 82 which is positioned on a lower side as flat surfaces which are inclined symmetrically in a vertical direction with respect to a bottom line 83 (indicated by a broken line in FIG. 11A) corresponding to a groove bottom portion.

A groove depth of the helical groove 80 is set such that circular arcuate surfaces 91 on the distal ends of the projections 90 formed on the syringe holding cylinder 20 described later are brought into point contact with the upper tapered surface 81 and/or the lower tapered surface 82.

On the other hand, the projections 90 have a function as the above-mentioned male threaded portion 24. As shown in FIG. 10A to FIG. 11B, the projections 90 are formed in a projecting manner from an outer wall of the syringe holding cylinder 20 toward the outside in a radial direction of the syringe holding cylinder 20 in a state where a distal end surface of the projection 90 which oppositely faces the helical groove 80 forms the circular arcuate surface 91.

In other words, each projection 90 projects from the outer peripheral surface of the syringe holding cylinder 20 such that the projection 90 has a circular arcuate surface 91 using the upper and lower tapered surfaces 81, 82 as tangents as viewed in cross section as shown in FIG. 11A and FIG. 11B, and makes the circular arcuate surface 91 face the upper tapered surface 81 and/or the lower tapered surface 82.

It is sufficient for the projection 90 to have the circular arcuate surface 91 which can be brought into slide contact with the upper and lower tapered surfaces 81, 82 of the helical groove 80 on a distal end thereof using the upper and lower tapered surfaces 81, 82 as the tangents. Accordingly, the projection 90 may be formed in a mushroom shape or in a shape where a distal end of the projection 90 is branched.

For example, as shown in FIG. 11A, the projection 90 may be formed in a spherical segment shape obtained by cutting out a spherical shape along an approximately one plane as a semispherical shape, a cutout portion of the spherical segment shape may be formed as a mounting base portion 93 for mounting the projection 90 on the outer periphery of the syringe holding cylinder 20, and spherical body portion of the spherical segment shape may be formed as a contact head portion 93 having a circular arcuate surface 91 which is brought into point contact with the upper and lower tapered surfaces 81, 82 of the helical groove 80.

As another example, as shown in FIG. 11B, the projection 90 may also be formed in an approximately capsule shape as the semispherical shape, a circular columnar portion of the capsule shape may be formed as a mounting base portion 92 for mounting and fixing the projection 90 to the outer peripheral surface of the syringe holding cylinder 20, and a semispherical portion of the capsule shape may be formed as a contact head portion 93 having a circular arcuate surface 91 which is brought into point contact with the upper and lower tapered surfaces 81, 82 of the helical groove 80.

The plurality of projections 90 are formed on the outer peripheral surface 20a of the syringe holding cylinder 20 such that the projections 90 can be brought into slide contact with the helical groove 80. To be more specific, the plurality of projections 90 are intermittently disposed on the outer peripheral surface 20a of the syringe holding cylinder 20 corresponding to the helical track 16.

In other words, the plurality of projections 90 which are disposed on the track of the outer peripheral surface 20a of the syringe holding cylinder 20 corresponding to the helical groove 80 of the outer cylinder 10 form a helical ridge which forms the male threaded portion 24 as shown in FIG. 10A and FIG. 10B.

An arrangement interval of the plurality of projections 90 may not be fixed provided that the plurality of projections 90 is threadedly engageable with the helical groove 80 of the outer cylinder 10, that is, the male threaded portion 24. In this embodiment, the plurality of projections 90 are disposed on the outer peripheral surface 20a of the syringe holding cylinder 20 at fixed intervals as shown in FIG. 10A.

As the above-mentioned multiple threads structure, the first male threaded portion 24a, the second male threaded portion 24*b*, and the third male threaded portion 24*c* respectively corresponding to the plurality of helical grooves 80 formed on the inner peripheral surface of the outer cylinder 10, that is, the first female threaded portion 17*a*, the second female threaded portion 17*b*, and the third female threaded portion 17*c* may be formed by arranging the plurality of projections 90 on the outer peripheral surface 20*a* of the syringe holding cylinder 20 as shown in FIG. 10B.

As an idea, such projections 90 may be mounted on the outer peripheral surface 20*a* of the syringe holding cylinder 20 in a rotatable manner about a rotation axis directed in the radial direction of the syringe holding cylinder 20.

As still another modification, the turning and helical advancing of the syringe holding cylinder 20 may be realized by bringing a helical ridge which is formed on an outer peripheral surface 20*a* of the syringe holding cylinder 20 (syringe holding cylinder body 22) into slide contact with a helical groove 51 which forms a helical track 16 formed on an inner peripheral surface of the outer cylinder 10.

That is, as an idea, it is also considerable that while the upper and lower tapered surfaces 81, 82 which expand inward in the radial direction of the outer cylinder 10 are formed on the helical groove 80, a helical ridge having a semicircular shape as viewed in cross section is formed contiguously, and the helical ridge is brought into line contact with the tapered surfaces 81, 82 thus reducing a sliding resistance at the time of turning and helically advancing the syringe holding cylinder 20.

[4. Injection Needle Removal Device According to Third Embodiment]

Figure 12:
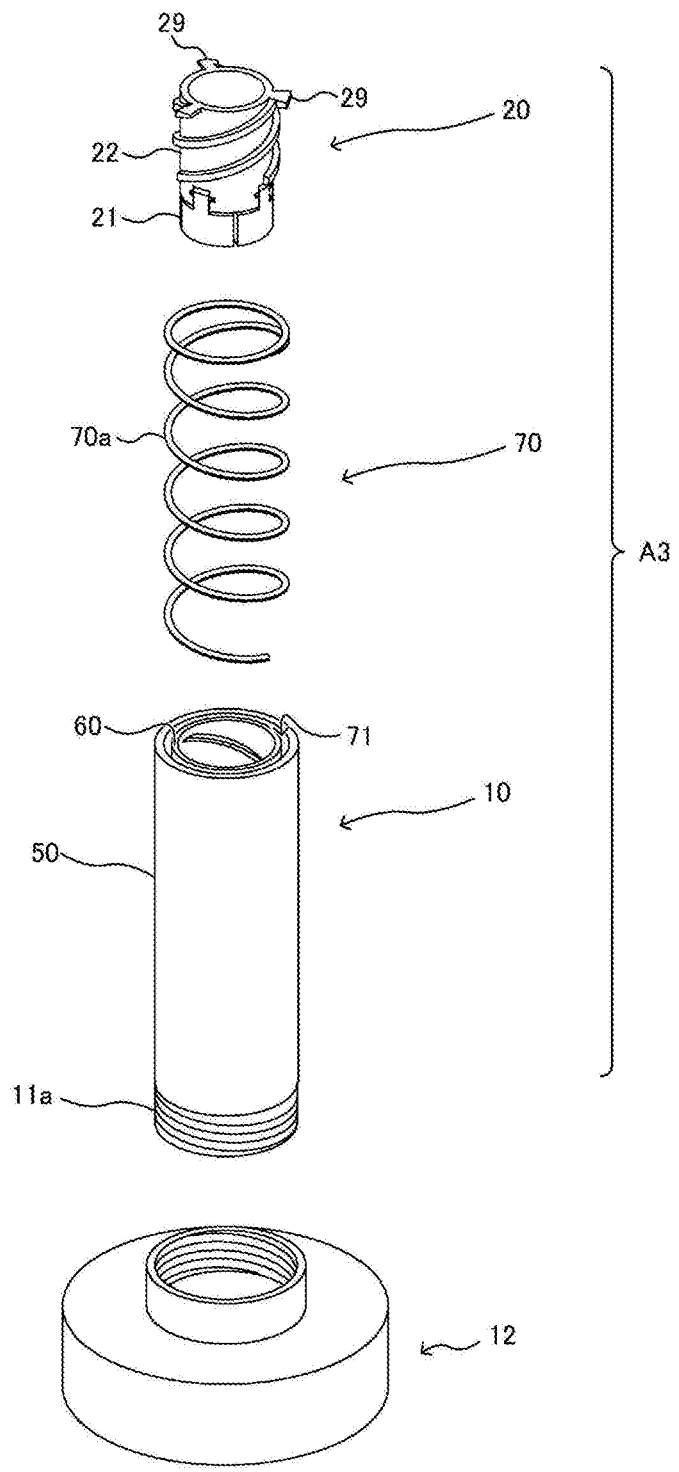
FIG. 12 is an exploded perspective view showing an injection needle removal device according to a third embodiment.
Figure 14:
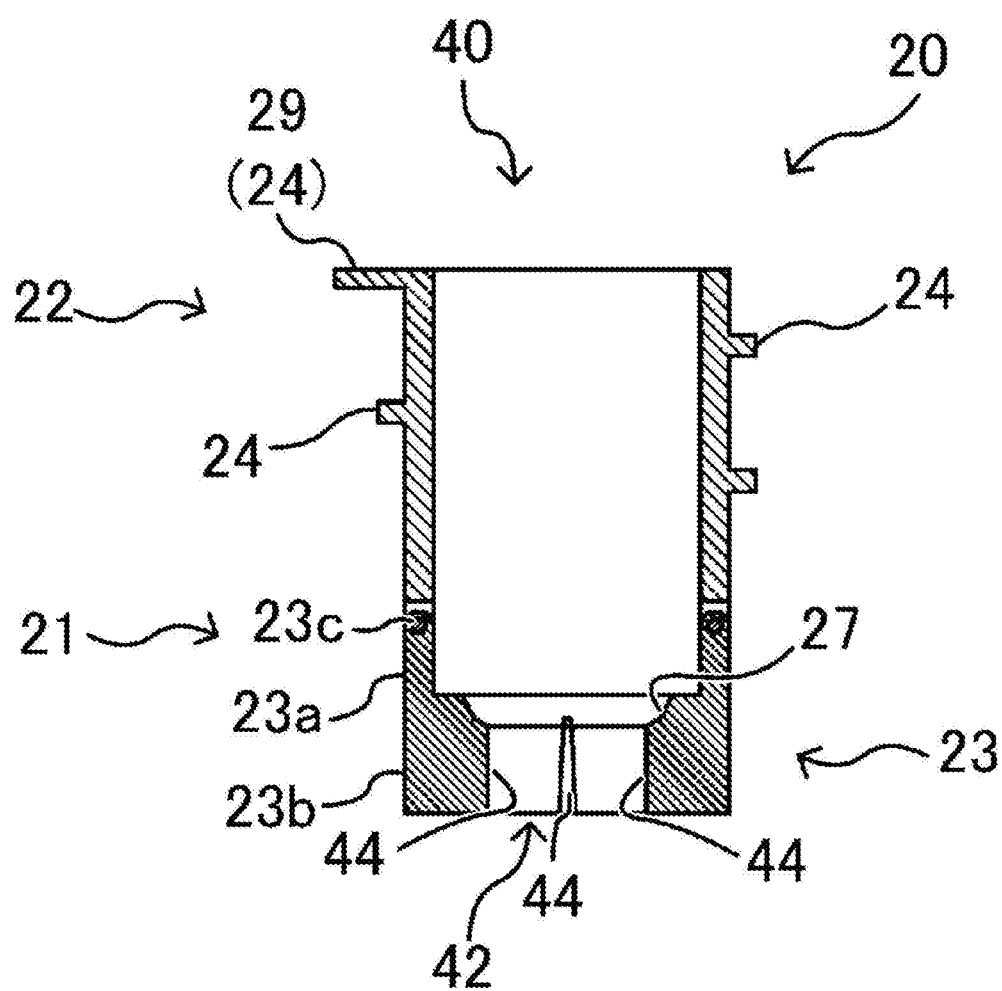
FIG. 14 is an explanatory view showing a syringe holding cylinder of the injection needle removal device according to the third embodiment.
Figure 15:
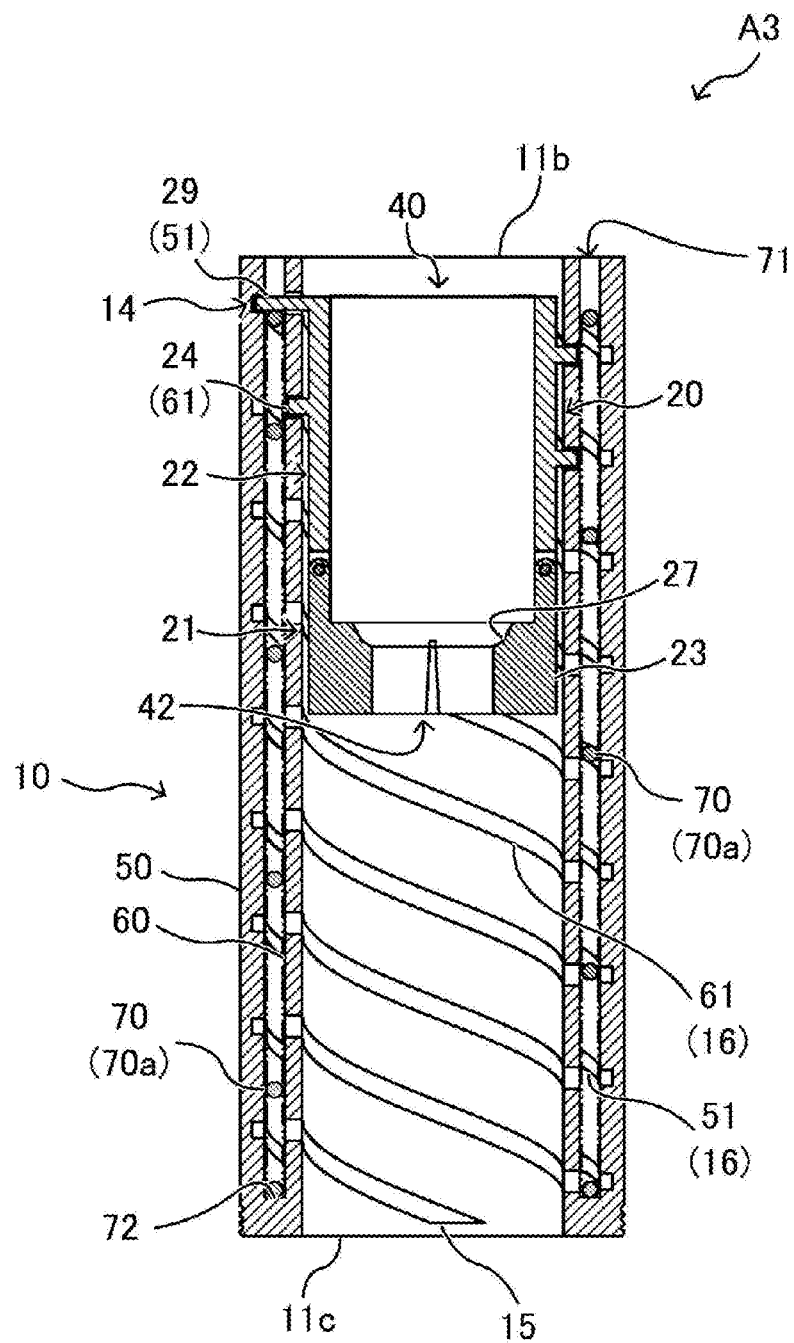
FIG. 15 is a cross-sectional view showing a configuration of the injection needle removal device according to the third embodiment.
Figure 16A:
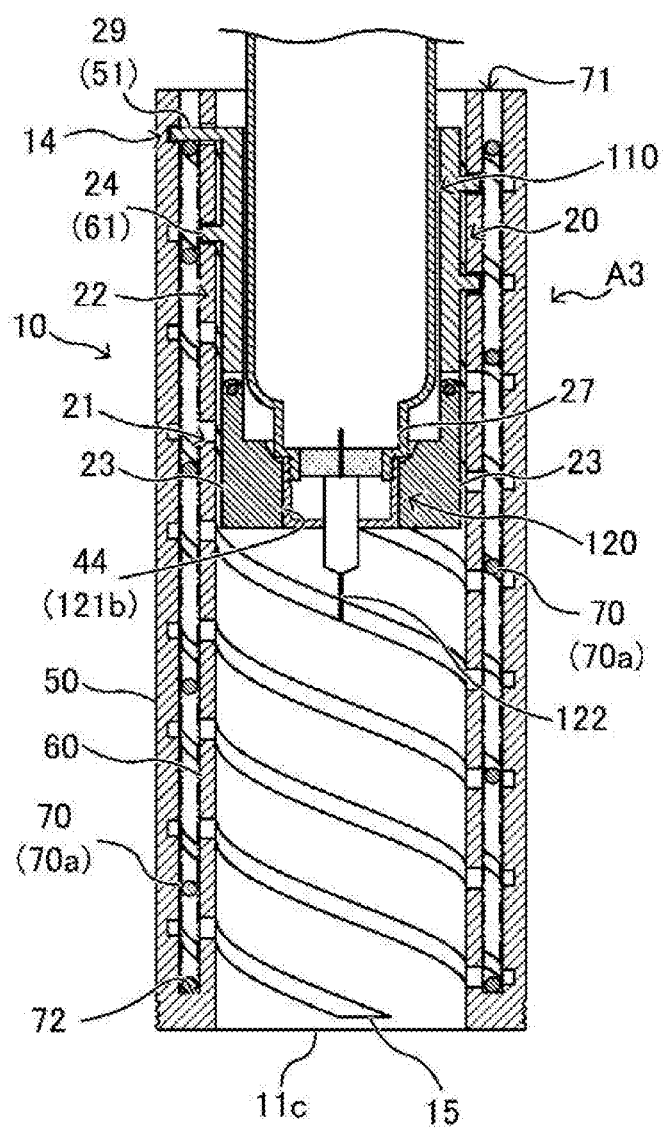
FIG. 16A, 16B, 16C are explanatory views showing a step of threadedly removing an injection needle of the injection needle removal device according to the third embodiment.
Figure 16B:
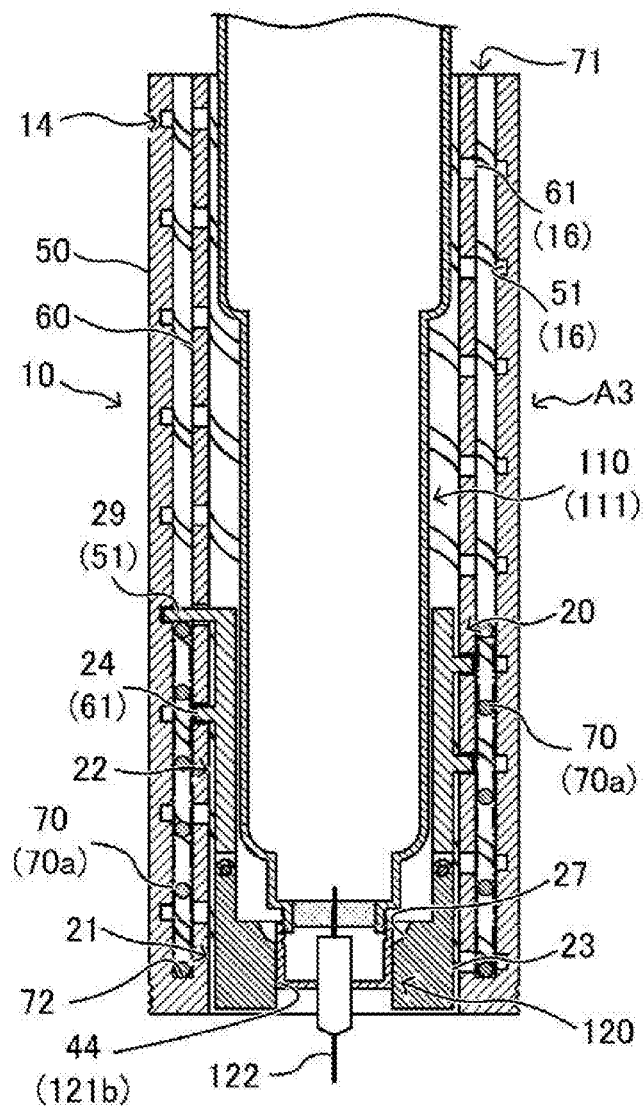
Figure 16C:
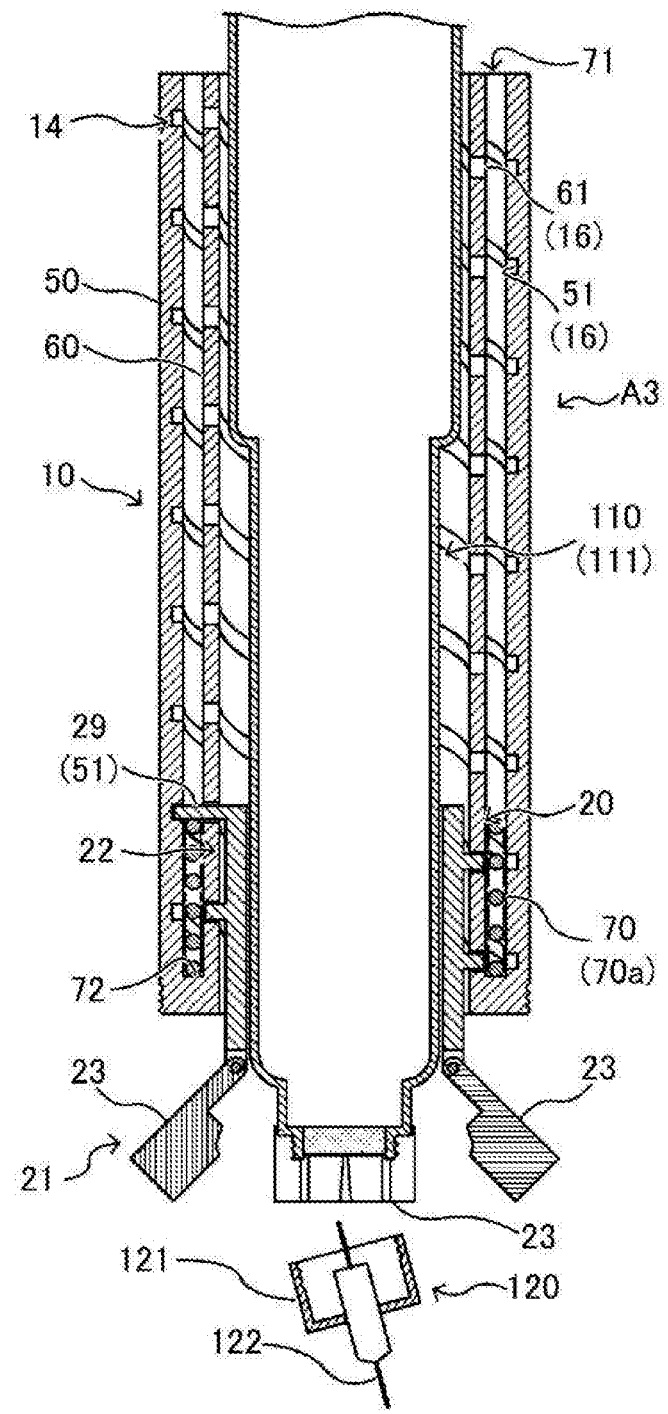

Next, an injection needle removal device according to a third embodiment is described in detail. FIG. 12 is an exploded perspective view of the injection needle removal device according to the third embodiment, FIG. 14 is a longitudinal cross-sectional view of a syringe holding body, FIG. 15 is a longitudinal cross-sectional view of the injection needle removal device, and FIG. 16A-16C are longitudinal cross-sectional views showing a step of threadedly removing an injection needle using the injection needle removal device. In the description made hereinafter, constitutional elements having substantially the same configurations as the corresponding constitutional elements of the above-mentioned injection needle removal device A1 are given the same symbols, and their description is omitted.

Figure 13:
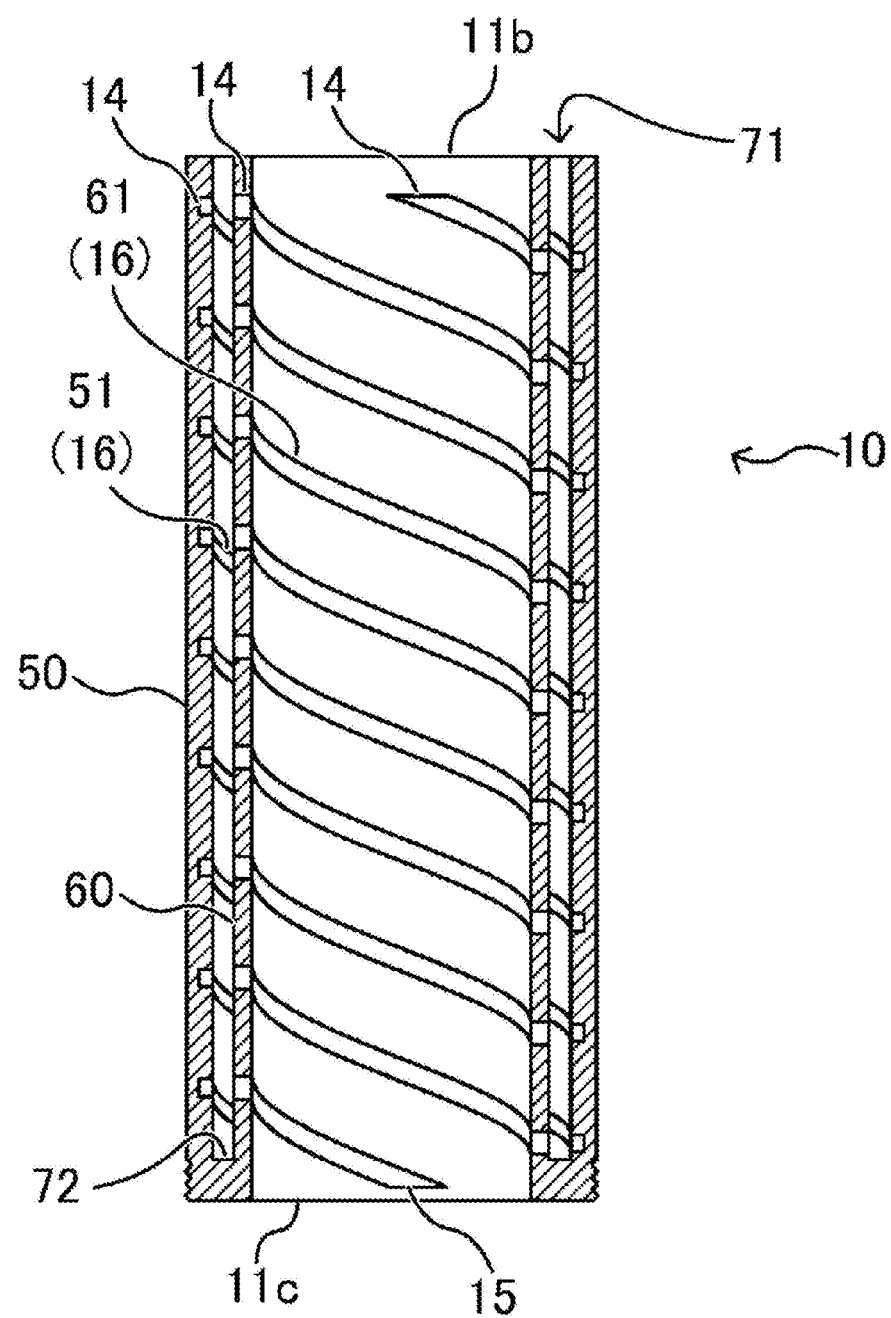
FIG. 13 is an explanatory view showing an internal configuration of an outer cylinder of an injection needle removal device according to the third embodiment.

As shown in FIG. 13, the outer cylinder 10 has an inner and outer double wall structure formed of an outer cylinder 50 and an inner cylinder 60 which are disposed on the same axis with a fixed distance therebetween.

Further, a lower edge of the outer cylinder 50 and a lower edge of the inner cylinder 60 are connected to each other by a horizontal lower locking flange 72 so that a space between the outer cylinder 50 and the inner cylinder 60 is formed in a bottomed shape thus forming an elastic body arranging space 71 where an elastic body 70 which constantly biases the syringe holding cylinder 20 in an upward direction is disposed.

As the elastic body 70, any member can be adopted provided that the member can be disposed in the elastic body arranging space 71, and the member can generate a biasing force for returning the syringe holding cylinder 20 upward. In this embodiment, a coil spring 70*a* is adopted.

As shown in FIG. 13, in the outer cylinder 10, a helical groove 51 is formed on an inner peripheral surface of the outer cylinder 50, and a helical slit 61 is formed in an inner wall of the inner cylinder 60 corresponding to the helical groove 51 of the outer cylinder 50.

That is, a helical track 16 (female threaded portion 17) of the outer cylinder 10 is formed of: the helical groove 51 which is formed on the inner peripheral surface of the outer cylinder 50; and the helical slit 61 which is formed in the peripheral wall of the inner cylinder 60 in a penetrating manner corresponding to the helical groove 51.

Opposite to the above-mentioned embodiment 1, the helical track 16 is formed such that the helical direction of the helical track 16 becomes the helical direction that the injection needle base portion 120 is threadedly removed from the syringe body 110 when the syringe holding cylinder 20 performs a turning and descending movement.

As shown in FIG. 12 and FIG. 14, a syringe holding cylinder 20 is formed such that a thickness of a wall portion of the syringe holding cylinder body 22 is made smaller by an amount that a thickness of the outer cylinder 10 is increased to have the double wall structure. To be more specific, the wall portion of the syringe holding cylinder body 22 is formed to have substantially the same thickness as a ring-use support projection 23*a* of a divided member 23.

Flange members 29 are formed on an upper end of the male threaded portion 24 which is formed on an outer peripheral surface of the syringe holding cylinder body 22. The flange members 20 are formed so as to extend toward the outside in the radial direction of the syringe holding cylinder 20 such that the flange members 29 engage with the helical groove 51 by fitting and are brought into slide contact with an upper end of the elastic body 70. In this embodiment, three flange members 29 are formed on the syringe holding cylinder 20 corresponding to the number of male threaded portions 24.

As shown in FIG. 15, the syringe holding cylinder 20 including such flange members 29 is disposed in the outer cylinder 10 such that the upper end of the elastic body 70 disposed in the elastic body arranging space 71 and the flange member 29 are brought into contact with each other.

To be more specific, in the syringe holding cylinder 20, the male threaded portion 24 threadedly engage with the helical slit 61 formed in the inner cylinder 60, and the flange member 29 formed on the upper end of the male threaded portion 24 is disposed such that the flange member 29 is positioned above the upper end of the elastic body 70 accommodated in the elastic body arranging space 71 and is brought into slide contact with the helical groove 51 formed on the outer cylinder 50 through the helical slit 61 formed in the inner cylinder 60.

In this manner, the injection needle removal device A3 has a biasing mechanism for biasing the syringe holding cylinder 20 upward in the outer cylinder 10 by interposing the elastic body 70 between the flange member 29 of the syringe holding cylinder 20 and an lower locking flange 72 of the outer cylinder 10 in the elastic body arranging space 71.

An engaging stepped portion 27 is formed on an end portion of an upper-end opening edge of a needle fitting mounting hole 42 formed in an injection needle tightening ring 21. To be more specific, the engaging stepped portion 27 is formed by cutting out upper ends of inner walls of ring-use spacer portions 23*b* of the plurality of divided members 23 which form the injection needle tightening ring 21 in a curved shape such that the engaging stepped portion 27 is brought into contact and engages with the front end edge of the cartridge 111.

Hereinafter, an in-use example of the injection needle removal device A3 is described in detail. In a unused state, as shown in FIG. 15, the injection needle removal device A3 is stopped such that the syringe holding cylinder 20 is biased upward in the outer cylinder 10 by the elastic body 70 so that the upper opening 41 of the fitting mounting hole 40 of the syringe holding cylinder body 22 is positioned at the position of the insertion opening 11b of the outer cylinder 10.

That is, the syringe holding cylinder 20 is biased upward in the outer cylinder 10 by the elastic body 70 by way of the flange member 29 and, at the same time, since the flange member 29 impinges on the upper locking point 14 of the helical track 16, the syringe holding cylinder 20 is stopped in a state where the upper opening 41 faces upward at an upper position in the outer cylinder 10.

Next, as shown in FIG. 16A, the user P inserts the syringe body 110 and the injection needle base portion 120 into the fitting mounting hole 40 of the syringe holding cylinder 20 in a stopped state in the outer cylinder 10.

To be more specific, in the injection needle tightening ring 21 which is formed of the plurality of divided members 23 which are supported by the inner peripheral surface of the outer cylinder 10 and gathered in a bud shape, a distal end edge of a cartridge 111 of the syringe body 110 is brought into contact with the engaging stepped portion 27, and the injection needle base portion 120 engage with the needle fitting mounting hole 42 by fitting.

Next, along with an operation of downwardly pressing the syringe body 110 against an upward biasing force of the elastic body 70 performed by the user P, the syringe holding cylinder 20 starts the turning and descending movement along the helical track 16 of the outer cylinder 10.

Along with the turning and descending movement of the syringe holding cylinder 20, the flange member 29 disposed on an upper end of the male threaded portion 24 is contracted by pressing the elastic body 70 which is disposed between the upper flange member 29 and the lower locking flange 72 in the elastic body arranging space 71 from above.

The injection needle base portion 120 which is held by being clamped by the injection needle tightening ring 21 in the needle fitting mounting hole 42 is rotated in a releasing direction with respect to the syringe body 110, and as shown in FIG. 16B, the injection needle base portion 120 is started to be gradually removed from the syringe body 110, and finally, the injection needle base portion 120 is completely threadedly removed from the syringe body 110.

When the user P further performs the downwardly pressing operation of the syringe body 110, the syringe holding cylinder 20 which performs the turning and descending movement is stopped in a state where the injection needle tightening ring 21 is exposed from a lower side of the outer cylinder 10 due to a stop mechanism of the syringe holding cylinder 20 where the lower end of the male threaded portion 24 of the syringe holding cylinder body 22 impinges on a lower locking point 15 of the outer cylinder 10 so that the movement of the syringe holding cylinder 20 is locked.

Due to a reaction of stopping the turning and ascending movement of the syringe holding cylinder 20 by such a stop mechanism, a turning and rotating stress of the syringe holding cylinder 20 is transmitted to the plurality of divided members 23.

As a result, as shown in FIG. 16C, the respective divided members 23 are swung outward due to a rotational stress and are formed into a blossomed state thus forming the injection needle tightening ring 21 where the distal end of the injection needle tightening ring 21 are divided and expanded, and the injection needle tightening ring 21 discards the injection needle base portion 120 which the injection needle tightening ring 21 holds while clamping in the injection needle accommodation case 30.

When the user P removes the syringe 100 from the injection needle removal device A3, the elastic body 70 which is in a contracted state by being pressed downwardly by the flange member 29 is released between the flange member 29 and the lower locking flange 72 and hence, an extension of the elastic body 70 is restored so that an upwardly biasing force is generated.

Accordingly, the upwardly biasing force of the elastic body 70 is transmitted to the syringe holding cylinder 20 by way of the flange member 29, the syringe holding cylinder 20 performs the turning and ascending movement due to the upwardly biasing force of the elastic body 70, and the syringe holding cylinder 20 returns to the position on an upper side in the outer cylinder 10 as shown in FIG. 15.

In this manner, the injection needle removal device A3 according to this embodiment is configured as a so-called depression-type injection needle removal device where, in the helical track 16 of the outer cylinder 10, while a turning and ascending forward path of the syringe holding cylinder 20 is used as a removing and discarding path of the injection needle base portion 120 for removing the injection needle base portion 120 from the syringe body 110 and for discarding injection needle base portion 120 into the injection needle accommodation case 30, a turning and ascending return path of the syringe holding cylinder 20 is used as a return path of the syringe holding cylinder 20 for returning the syringe holding cylinder 20 to the upper position in the outer cylinder 10 using the biasing mechanism.

[5. Injection Needle Removal Device According to Fourth Embodiment]

Figure 18:
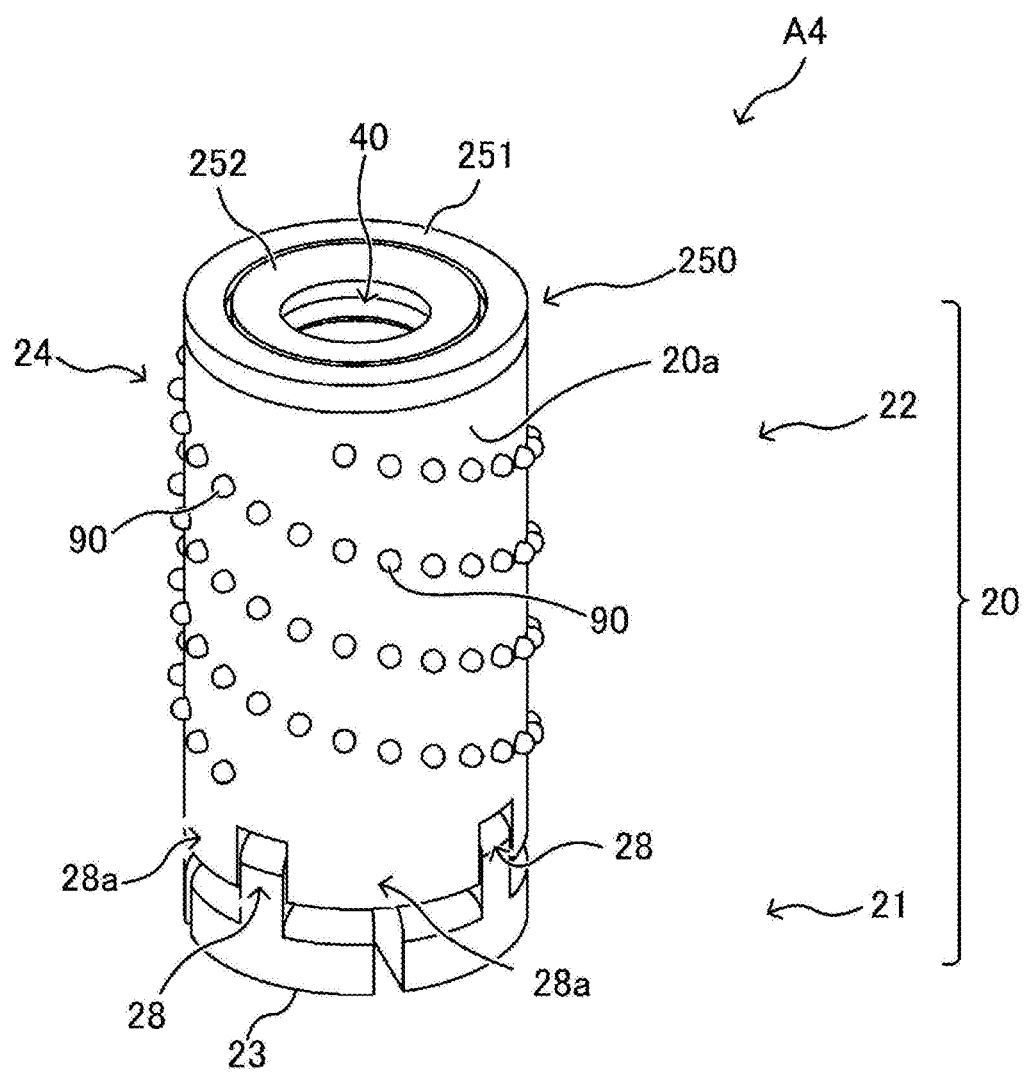
FIG. 18 is an external appearance perspective view showing a configuration of a syringe holding cylinder of an injection needle removal device according to a fourth embodiment.
Figure 19:
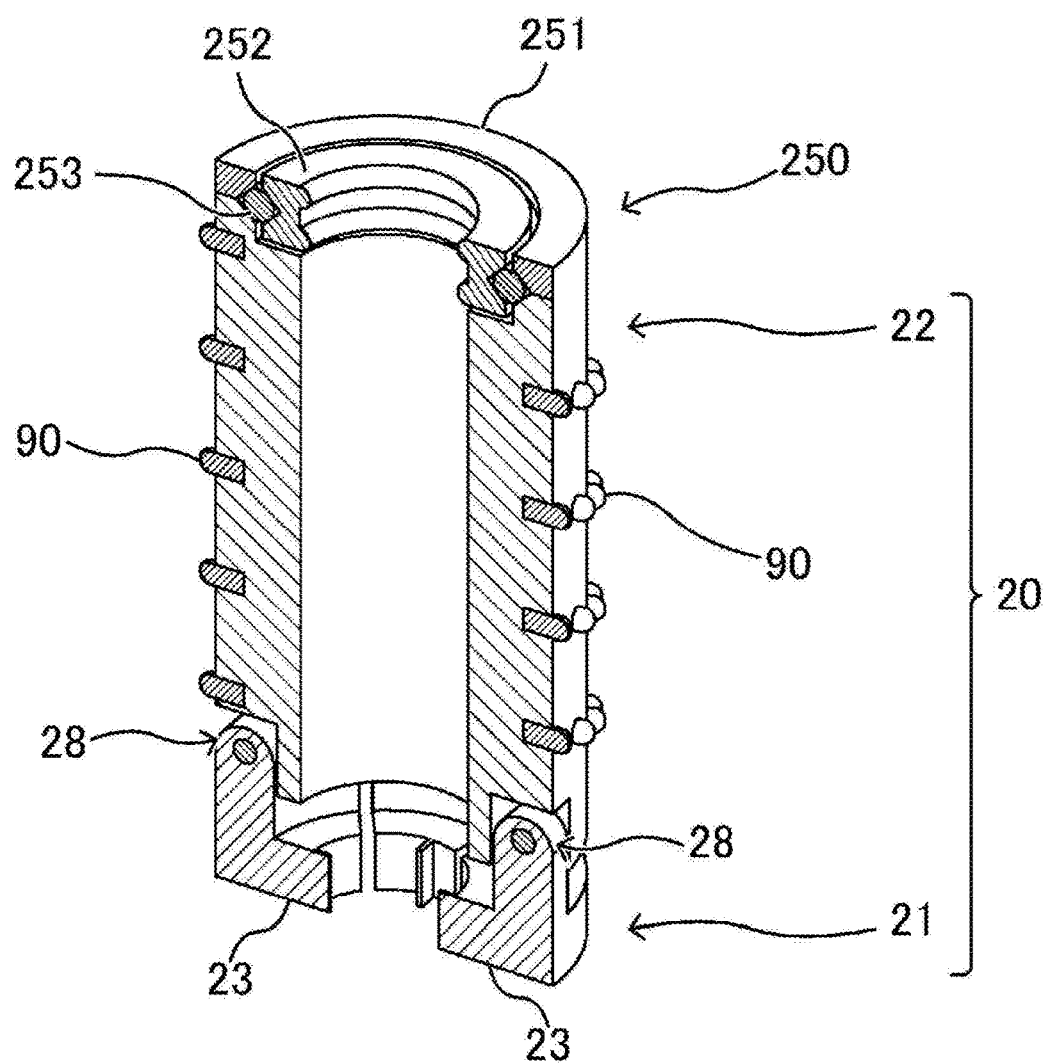
FIG. 19 is a cross-sectional perspective view showing a configuration of the syringe holding cylinder of the injection needle removal device according to the fourth embodiment.
Figure 20:
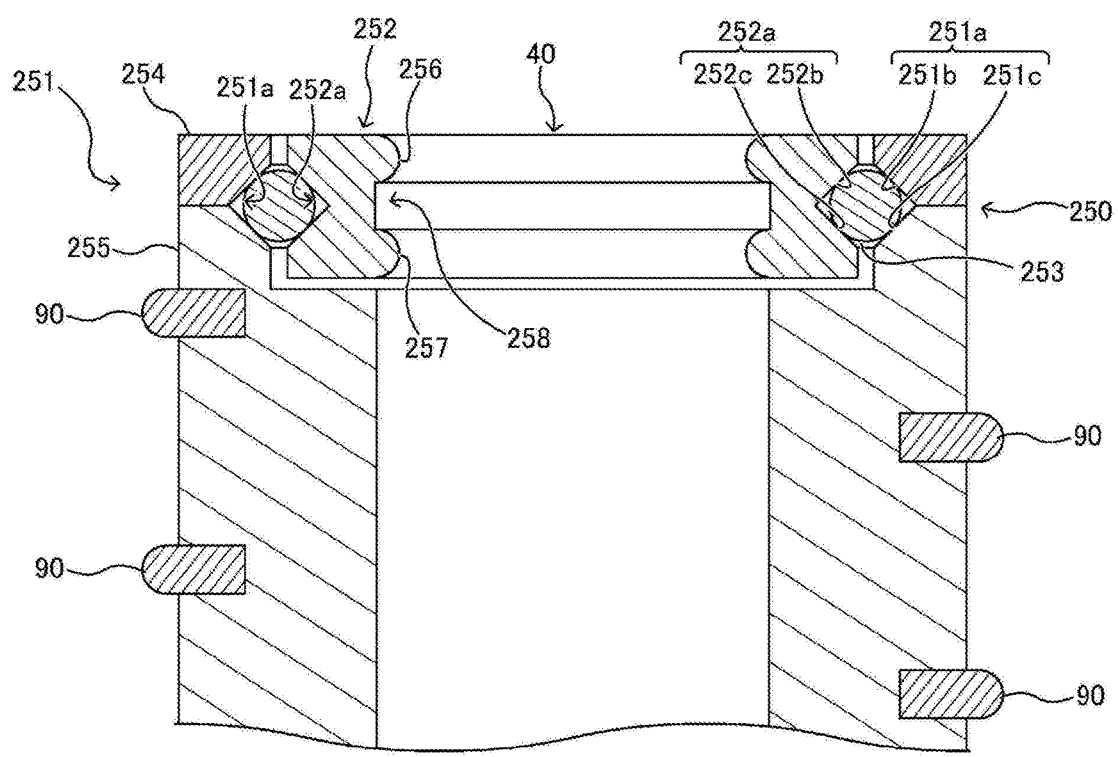
FIG. 20 is a side cross-sectional view showing the configuration of the syringe holding cylinder of the injection needle removal device according to the fourth embodiment.
Figure 21:
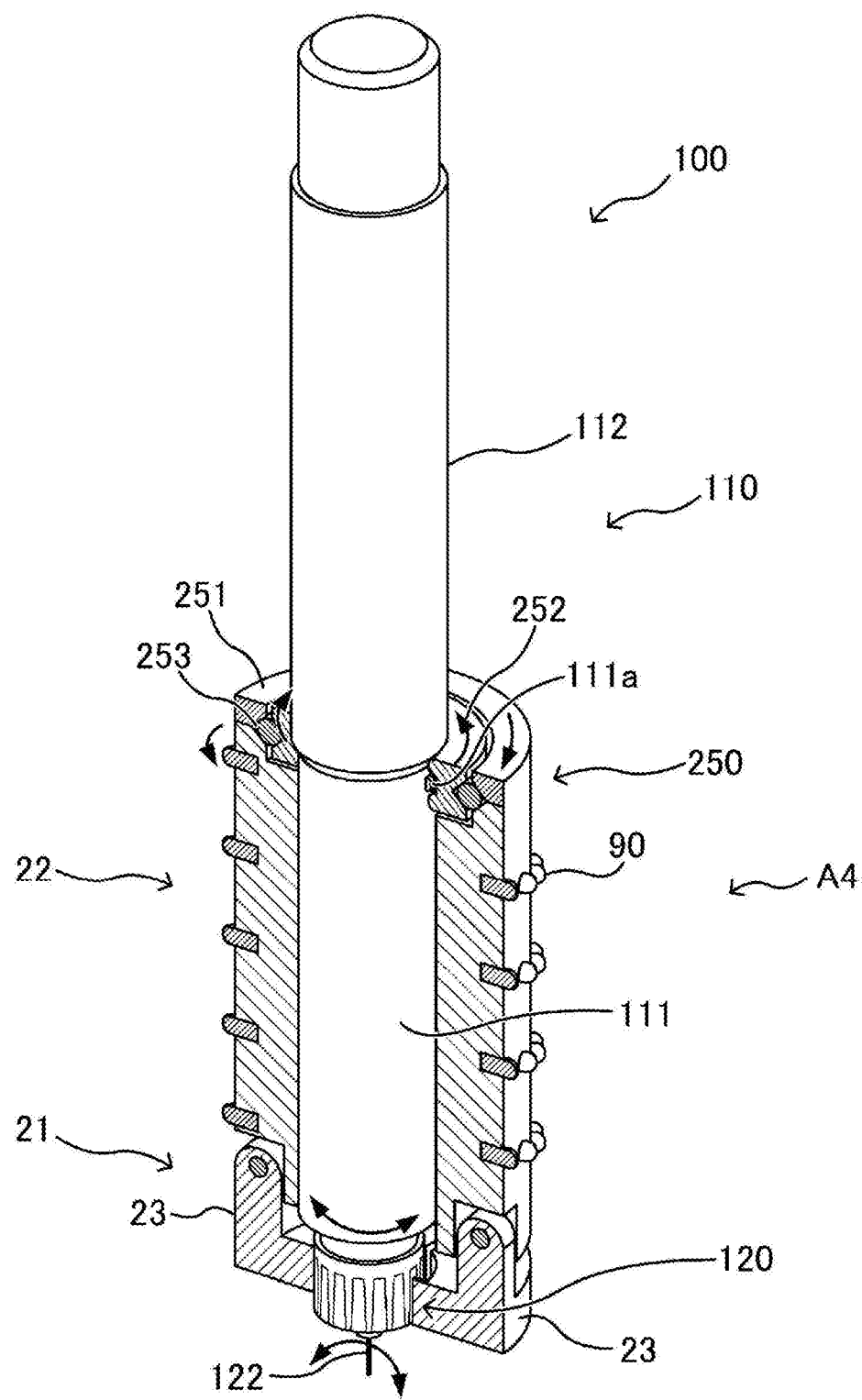
FIG. 21 is a cross-sectional perspective view showing a state where a syringe is inserted into the syringe holding cylinder of the injection needle removal device according to the fourth embodiment.
Figure 22:
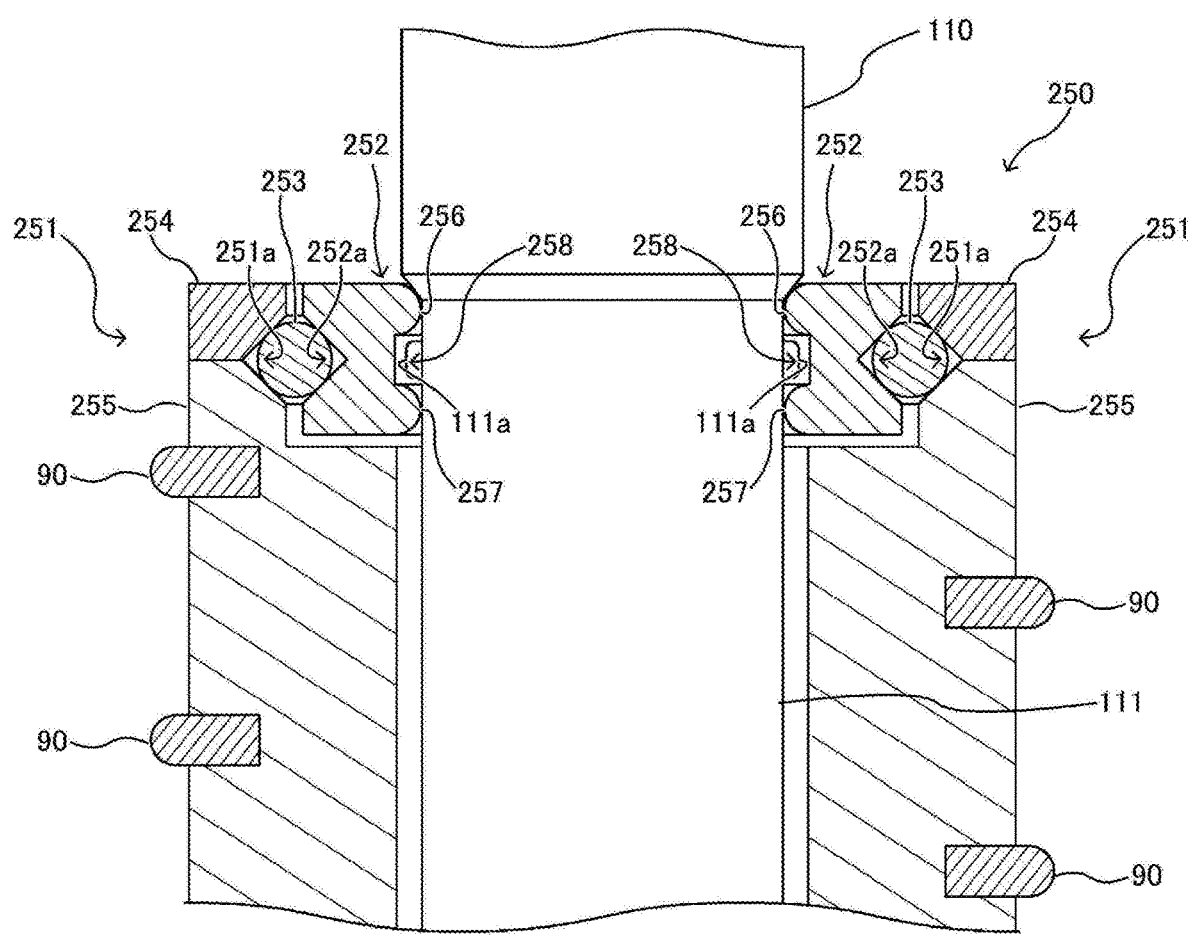
FIG. 22 is a side cross-sectional view showing a state where the syringe is inserted into the syringe holding cylinder of the injection needle removal device according to the fourth embodiment.

Next, an injection needle removal device according to a fourth embodiment is described in detail. FIG. 18 is an external appearance perspective view showing a configuration of the syringe holding cylinder according to the fourth embodiment, FIG. 19 is a cross-sectional perspective view showing a configuration of a syringe holding cylinder, FIG. 20 is a transverse cross-sectional view showing a configuration of the syringe holding cylinder, FIG. 21 is a cross-sectional perspective view showing a state where a syringe is inserted into the syringe holding cylinder, and FIG. 22 is a transverse cross-sectional view showing a state where the syringe is inserted into the syringe holding cylinder. In the drawings, the illustration of the outer cylinder 10 is omitted.

The injection needle removal device A4 according to the fourth embodiment is configured to perform an operation of pulling up a syringe holding cylinder body 22 by making use of projections 111a which project from an upper outer peripheral surface of a cartridge 111 at the time of performing a pull-up operation of a syringe body 110.

The injection needle removal device A4 is configured such that when the syringe holding cylinder body 22 is rotated through the threaded engagement between the syringe holding cylinder body 22 and the outer cylinder 10, and a lower end of the syringe holding cylinder body 22, that is, injection needle base portion 120 clamped by the injection needle tightening ring 21 is rotated for threadedly removing the injection needle base portion 120 at a lower end of the syringe body 110 thus removing the injection needle 122, the syringe holding cylinder body 22 can be smoothly rotated inside the outer cylinder 10 due to a bearing structure.

As shown in FIG. 18 and FIG. 19, the bearing structure which forms a grip means 250 is disposed in an interposed manner between an expanded inner peripheral wall portion 251 which is formed by expanding an inner peripheral wall on an upper end portion of a syringe holding cylinder 20 toward the outer periphery and a syringe holding inner race 252 which is loosely fitted in the expanded inner peripheral wall portion 251. In other words, the bearing structure which forms the grip means 250 is provided such that the syringe holding inner race 252 is loosely fitted and supported by the expanded inner peripheral wall portion 251 with rolling bodies 253 interposed therebetween.

To be more specific, the bearing structure includes the expanded inner peripheral wall portion 251 on an upper end portion of the syringe holding cylinder 20 and the syringe holding inner race 252 which is disposed concentrically with the expanded inner peripheral wall portion 251 and is loosely fitted in the expanded inner peripheral wall portion 251 in a rotatable manner in a circumferential direction of the syringe holding cylinder 20 by way of the plurality of rolling bodies 253. The rolling body 253 may be formed of a true spherical ball or a roller having a roller shape, and the plurality of rolling bodies are disposed at predetermined intervals in the circumferential direction.

As shown in FIG. 20, an outer race recessed groove 251a is formed on the inner periphery of the expanded inner peripheral wall portion 251. Further, an inner race recessed groove 252a is formed on the outer periphery of the syringe holding inner race 252 corresponding to the outer race recessed groove 251a of the expanded inner peripheral wall portion 251. Upper and lower tapered surfaces 251b, 251c are respectively formed on the respective recessed grooves 251a, 252a, 252b, 252c which are inclined so as to oppositely face each other in an expanding direction as viewed in transverse cross section.

As viewed in a side view, the expanded inner peripheral wall portion 251 is formed of: a ring-shaped closing lid portion 254 having the upper tapered surface 251b which is a tapered surface formed by inclining a lower end inner peripheral surface of the expanded inner peripheral wall portion 251; and an expanded inner peripheral wall main body portion 255 having the lower tapered surface 251c on an upper end of the syringe holding cylinder body 22.

As shown in FIG. 19 and FIG. 20, the syringe holding inner race 252 has a ring shape having a large wall thickness and is brought into contact with the outer periphery of the cartridge 111 at the inner periphery thereof. On inner periphery upper and lower end edges of the syringe holding inner race 252, two flange engaging portions, that is, upper and lower flange engaging portions 256, 257 having a large wall thickness are formed in a pleat shape in an inwardly projecting manner respectively. On an inner periphery center portion of the syringe holding inner race 252, an engaging recessed portion 258 in which projections 111a are fitted is formed by two upper and lower flange engaging portions 256, 257.

Flange head portions of the upper and lower flange engaging portions 256, 257 are formed in a rounded shape so that a peripheral-surface friction resistance with the cartridge 111 can be reduced as much as possible. A cutout portion not shown in the drawing which allows the projections 111a to be inserted into the engaging recessed portion 258 is formed on an inner peripheral edge of the upper flange engaging portion 256.

The projections 111a of the syringe body 110 which is positioned by being fitted in the engaging recessed portion 258 of the syringe holding cylinder body 22 impinge on and are brought into contact with the upper and lower flange engaging portions 256, 257 as shown in FIG. 21 and FIG. 22 and hence, a stress in the vertical direction of the syringe body 110 is transmitted to the syringe holding cylinder 20.

The syringe holding cylinder 20 which moves in the vertical direction moves in a rotatable manner by converting a stress in the vertical direction into a rotational stress by the helical track 16 in the outer cylinder 10. However, the syringe holding inner race 252 which holds the syringe body 110 is rotatable with respect to the expanded inner peripheral wall portion 251 of the syringe holding cylinder body 22 by way of the roller bodies 253 and hence, there is no possibility that the syringe holding inner race 252 transfers a rotational stress from the syringe holding cylinder body 22 to the syringe body 110.

In other words, a rotational stress of the syringe holding cylinder 20 is transmitted only to the injection needle base portion 120 which is clamped by the injection needle tightening ring 21 on the lower end of the syringe holding cylinder 20 without being transmitted to the syringe body 110 from the syringe holding cylinder body 22 by the bearing structure of the grip means 250.

Accordingly, the injection needle removal device A4 can remove the injection needle 122 together with the injection needle base portion 120 from the syringe body 110 by rotating only the injection needle base portion 120 while keeping a non-movable state of the syringe body 110 in a rotational direction.

In the case where the projections 111a are not provided to the cartridge 111 of the syringe 100, substantially the same injection needle removal operation can be realized by forming the syringe holding inner race 252 using an elastic material such as a resin, for example. To be more specific, the upper and lower flange engaging portions 256, 257 (syringe holding inner race 252) are formed to have a flange inner diameter slightly smaller than an outer diameter of the cartridge 111 using an elastic material.

That is, while the syringe holding cylinder 20 can grip the syringe body 110 tightly by generating a high frictional force by the grip means 250 with respect to a stress in the vertical direction (axial direction) of the syringe holding cylinder 20, with respect to a stress in the rotational direction (circumferential direction) of the syringe holding cylinder 20, the syringe body 110 and the syringe holding cylinder 20 slide on each other by the grip means 250 and hence, the syringe body 110 is not rotated integrally with the injection needle base portion 120, and the injection needle 122 can be removed from the syringe body 110 together with the injection needle base portion 120 by rotating only the injection needle base portion 120.

It is needless to say that the above-mentioned first to fourth embodiments can be carried out even when the configurations of the embodiments are exchanged with each other, and in such a case, it is possible to acquire the same manner of operation and advantageous effects.

Finally, the above-mentioned respective embodiments merely show one example of the present invention, and the present invention is not limited to the above-mentioned embodiments. Accordingly, it is needless to say that, besides the above-mentioned respective embodiments, various modifications are conceivable corresponding to designs and the like without departing from the technical concept of the present invention.

REFERENCE SIGNS LIST

A1 injection needle removal device
10 outer cylinder
14 upper locking point
15 lower locking point
16 helical track
20 syringe holding cylinder
21 injection needle tightening ring
30 injection needle accommodation case
100 syringe
110 syringe body

The invention claimed is:

1. An injection needle removal device, comprising:
a cylindrical outer cylinder that is mountable on an upper opening of an injection needle accommodation case;
a helical track that is formed on an inner peripheral surface of said outer cylinder in a helical shape from an upper locking point to a lower locking point;
a syringe holding cylinder having a cylindrical shape that turns and helically advances in said outer cylinder along said helical track;
an injection needle tightening ring, which is disposed on a lower end portion of the syringe holding cylinder that is capable of holding an injection needle base portion of a syringe inserted into said syringe holding cylinder while clamping said injection needle base portion;
a locking mechanism which stops said syringe holding cylinder in a state where said injection needle tightening ring is exposed from a lower side of said outer cylinder at said lower locking point; and
wherein said injection needle tightening ring is configured to remove said injection needle base portion from a syringe body due to turning of said syringe holding cylinder, and to expand in a distal-end divided manner due to a turning force generated by a descending movement of said syringe holding cylinder in a vicinity of said lower locking point thus discarding said injection needle base portion into said injection needle accommodation case together with said injection needle.

2. The injection needle removal device, according to claim 1, wherein:
turning and helical advancing of said syringe holding cylinder is realized by bringing a projection formed on an outer peripheral surface of said syringe holding cylinder into a slide contact with a helical groove which is formed on an inner peripheral surface of said outer cylinder as a helical track, and
upper and lower tapered surfaces, which are expanded inwardly in a radial direction of the outer cylinder, are formed on the helical groove, and a projection is formed of a projection having a circular arcuate surface on a distal end thereof, and said projection is brought into point contact with said tapered surfaces so as to reduce a sliding resistance generated at the time of helically turning advancing said syringe holding cylinder is reduced.

3. The injection needle removal device, according to claim 2, wherein:
said projection is formed of a plurality of projections, which are formed on said outer peripheral surface of said syringe holding cylinder, and a plurality of projections is brought into slide contact with said helical groove.

4. The injection needle removal device, according to claim 1, wherein:
said injection needle tightening ring is formed of a plurality of divided members that are pivotally mounted on a lower portion of a cylindrical syringe holding cylinder body that forms said syringe holding cylinder in an expandable manner.

5. The injection needle removal device, according to claim 1, wherein:
a grip means that generates a friction force against an operation of removing said syringe body from the syringe holding cylinder is provided to an inner wall of the syringe holding cylinder that faces opposingly said syringe body.

6. The injection needle removal device, according to claim 1, further comprising:
a biasing mechanism that biases said syringe holding cylinder upward in said outer cylinder.

7. The injection needle removal device, according to claim 6, wherein:
said outer cylinder has a double cylindrical structure formed of an outer cylinder and an inner cylinder disposed on a same axis;
said helical track is formed of a helical groove formed on an inner peripheral surface of said outer cylinder, and a helical slit formed in a peripheral wall of said inner cylinder in a penetrating manner corresponding to said helical groove;
said syringe holding cylinder has a flange member that is brought into slide contact with said helical groove through said helical slit, and
said biasing mechanism is configured to push up said flange member by an elastic body disposed in a space formed between said outer cylinder and said inner cylinder.

* * * * *